US011220710B2

(12) United States Patent
Oberstrass et al.

(10) Patent No.: US 11,220,710 B2
(45) Date of Patent: Jan. 11, 2022

(54) RNA SEQUENCING METHODS

(71) Applicant: Ultima Genomics, Inc., Newark, CA (US)

(72) Inventors: Florian Oberstrass, Menlo Park, CA (US); Gilad Almogy, Palo Alto, CA (US)

(73) Assignee: ULTIMA GENOMICS, INC., Newark, CA (US)

(*) Notice: Subject to any disclaimer, the term of this patent is extended or adjusted under 35 U.S.C. 154(b) by 0 days.

(21) Appl. No.: 17/158,960

(22) Filed: Jan. 26, 2021

(65) Prior Publication Data
US 2021/0147931 A1 May 20, 2021

Related U.S. Application Data

(63) Continuation of application No. PCT/US2020/041552, filed on Jul. 10, 2020.
(Continued)

(51) Int. Cl.
C12Q 1/6869 (2018.01)
C12Q 1/6874 (2018.01)
C12N 15/10 (2006.01)

(52) U.S. Cl.
CPC ....... C12Q 1/6869 (2013.01); C12N 15/1096 (2013.01); C12Q 1/6874 (2013.01);
(Continued)

(58) Field of Classification Search
None
See application file for complete search history.

(56) References Cited

U.S. PATENT DOCUMENTS 8,772,473 B2  7/2014  Huang
10,975,479 B2  4/2021  Fritz et al.
(Continued)

FOREIGN PATENT DOCUMENTS

WO  2020227161 A1  11/2020

OTHER PUBLICATIONS

Macosko et al., "Highly Parallel Genome-wide Expression Profiling of Individual Cells Using Nanoliter Droplets," Cell 2015, 161: 1202-1214. (Year: 2015).*
(Continued)

Primary Examiner — Kaijiang Zhang
(74) Attorney, Agent, or Firm — Morrison & Foerster LLP

(57) ABSTRACT

Described herein are methods for determining a sequence of a region of interest from an mRNA molecule. Sequenced polynucleotides can include a barcode region, a homopolymer region (e.g., a poly-A region), and a target region associated with the mRNA molecule. According to some methods, the barcode region omits the same base present in the homopolymer region. According to some methods, extension of the primer used for sequencing is stalled within the homopolymer region. According to some methods, sequencing flow cycles and the different barcode regions of the polynucleotides configured are such that the primer is extended to the end of the barcode region across the plurality of polynucleotides before being extended into the homopolymer region. According to some methods, two primers or a cleavable primer is used to separately sequence the barcode region and the target region.

20 Claims, 10 Drawing Sheets

Related U.S. Application Data

(60) Provisional application No. 62/872,558, filed on Jul. 10, 2019.

(52) U.S. Cl.
CPC .. *C12Q 2525/161* (2013.01); *C12Q 2525/173* (2013.01); *C12Q 2525/191* (2013.01); *C12Q 2563/179* (2013.01); *C12Q 2563/185* (2013.01); *C12Q 2600/178* (2013.01); *C12Y 207/07049* (2013.01)

(56) References Cited

U.S. PATENT DOCUMENTS

| | | |
|---|---|---|
| 2003/0119005 A1 | 6/2003 | Brush |
| 2005/0100932 A1 | 5/2005 | Lapidus et al. |
| 2015/0203887 A1 | 7/2015 | Lazinski |
| 2017/0314067 A1 | 11/2017 | Shum |
| 2019/0048335 A1 | 2/2019 | Li |
| 2019/0153520 A1 | 5/2019 | Barbee |
| 2019/0276942 A1 | 9/2019 | Fritz et al. |
| 2020/0372971 A1 | 11/2020 | Etzioni |
| 2020/0377937 A1 | 12/2020 | Pratt |
| 2020/0392584 A1 | 12/2020 | Almogy |
| 2021/0010075 A1 | 1/2021 | Oberstrass |
| 2021/0147930 A1 | 5/2021 | Oberstrass et al. |

OTHER PUBLICATIONS

Ivanov, I. E. et al. (Jan. 23, 2018). "Multimodal Measurements of Single-Molecule Dynamics Using FluoRBT," Biophysical Journal 114(2):278-282.

The International Search Report And Written Opinion Of The International Searching Authority dated Oct. 26, 2020, for International Patent Application No. PCT/US2020/041552, filed Jul. 10, 2020, 14 pages.

U.S. Appl. No. 17/086,203, filed May 1, 2020, by Mark Pratt, et al. (The U.S. Patent Application is not submitted herewith pursuant to the waiver of 37 C.F.R. § 1.98(a)(2)(iii) issued by the Office on Sep. 21, 2004).

U.S. Appl. No. 17/158,953, filed Jan. 26, 2021, by Florian Oberstrass et al. (The U.S. Patent Application is not submitted herewith pursuant to the waiver of 37 C.F.R § 1.98(a)(2)(iii) issued by the Office on Sep. 21, 2004).

\* cited by examiner

RNA SEQUENCING METHODS

CROSS-REFERENCE TO RELATED APPLICATION

This application is a continuation of International Application No. PCT/US2020/041552, filed on Jul. 10, 2020, which claims priority benefit to U.S. Provisional Application No. 62/872,558, filed Jul. 10, 2019, each of which is incorporated herein by reference for all purposes.

FIELD OF THE INVENTION

Described herein are methods for sequencing a region of interest within an mRNA molecule.

BACKGROUND

Messenger RNA (mRNA) sequencing can provide information about real-time gene expression, gene expression profiles in different tissues, and the level of gene expression. Variations in expression levels of particular genes can vary in response to environmental stimuli, during different developmental stages, or in a cause or effect relationship with disease.

Direct mRNA sequencing is challenging, and targeted mRNA molecules are typically reverse transcribed into complementary DNA (cDNA) molecules using reverse transcriptase. The cDNA molecules are then sequenced to provide sequencing information about the original mRNA molecule. Eukaryotic mRNA generally includes a poly(A) tail on the 3' end of the mRNA molecule, which is reflected by a poly(T) region at the 5' end of the cDNA molecule. Optionally, a complementary DNA strand to the cDNA molecule is synthesized, resulting in a poly(A) tail at the 3' end of the DNA molecule.

Certain highly efficient sequencing methods utilize non-terminating nucleotides to sequence nucleic acid molecules. These sequencing methods may be referred to as "flow sequencing," "natural sequencing-by-synthesis," or "non-terminated sequencing-by-synthesis" methods (see, for example, U.S. Pat. No. 8,772,473, which is incorporated herein by reference in its entirety).

BRIEF SUMMARY OF THE INVENTION

Described herein are methods of determining a sequence of a region of interest from an mRNA molecule.

In some embodiments, a method of determining a sequence of a region of interest from an mRNA molecule comprises (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, wherein the barcode region omits the same base present in the homopolymer region; (b) determining the sequence of the barcode region using labeled nucleotides that lack a complement base of the same base present in the homopolymer region; (c) extending the primer within the homopolymer region using nucleotides complementary to the base present in the homopolymer region; and (d) determining the sequence of the target region using labeled nucleotides. In some embodiments, the labeled nucleotides used in step (b) comprise non-terminating labeled nucleotides. In some embodiments, the nucleotides used in step (c) comprise non-terminating nucleotides. In some embodiments, the nucleotides used in step (d) comprise non-terminating labeled nucleotides. In some embodiments, the labeled nucleotides used in step (b) are mixed with unlabeled nucleotides of the same base. In some embodiments, the nucleotides complementary to the base present in the homopolymer region comprise unlabeled nucleotides. In some embodiments, the sequence of the target region is determined using a mixture of unlabeled nucleotides and the labeled nucleotides. In some embodiments, different bases of the labeled nucleotides used to determine the target region are discretely used. In some embodiments, different bases of the labeled nucleotides used to determine the barcode region are discretely used. In some embodiments, the target region of each polynucleotide is associated with a unique barcode region. In some embodiments, no more than 50% of the total nucleotides used in step (b), step (c), or step (d) are labeled. In some embodiments, no more than 0.1% of the total nucleotides used in step (c) are labeled. In some embodiments, the method further comprises repeating step (c) one or more times until the primer is extended to the end of the homopolymer region, wherein unincorporated nucleotides are removed between repeated steps.

In some embodiments, a method of determining a sequence of a region of interest from an mRNA molecule comprises: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides and unlabeled nucleotides at a first proportion of labeled nucleotides to total nucleotides; (c) extending the primer using labeled nucleotides complementary to the base present in the homopolymer region at a second proportion of labeled nucleotides to total nucleotides, wherein the second proportion of is greater than the first proportion, wherein primer extension stalls within the homopolymer region; (d) extending the primer to the end of the homopolymer region using unlabeled nucleotides complementary to the base present in the homopolymer region; and (e) determining the sequence of the target region using labeled nucleotides. In some embodiments, the labeled nucleotides and unlabeled nucleotides used in step (b) comprise non-terminating labeled nucleotides and non-terminating unlabeled nucleotides. In some embodiments, the labeled nucleotides used in step (c) comprise non-terminating labeled nucleotides. In some embodiments, the unlabeled nucleotides used in step (d) comprise non-terminating unlabeled nucleotides. In some embodiments, the labeled nucleotides used in step (e) comprise non-terminating labeled nucleotides. In some embodiments, the sequence of the target region is determined using labeled nucleotides and unlabeled nucleotides. In some embodiments, 50% or fewer of the nucleotides used in step (b) or (e) are labeled. In some embodiments, greater than 50% of the nucleotides used in step (c) are labeled. In some embodiments, 0.1% or fewer of the nucleotides used in step (d) are labeled. In some embodiments, all of the nucleotides used in step (d) are unlabeled. In some embodiments, step (d) comprises repeatedly removing unincorporated nucleotides and adding fresh nucleotides one or more times until the primer is extended to the end of the homopolymer region. In some embodiments, the target region of each polynucleotide is associated with a unique barcode region.

In some embodiments, different bases of the labeled nucleotides used to determine the target region are discretely used. In some embodiments, different bases of the labeled nucleotides used to determine the barcode region are discretely used.

In some embodiments, a method of determining a sequence of a region of interest from an mRNA molecule comprises: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, and wherein the target region is associated with a unique barcode region; (b) determining the sequence of the barcode region using labeled nucleotides in a plurality of predetermined cycles, wherein the predetermined cycles and the barcode regions of the polynucleotides are configured such that the primer is extended to the end of the barcode region across the plurality of polynucleotides before being extended into the homopolymer region; (c) extending the primer within the homopolymer region using unlabeled nucleotides; and (d) determining the sequence of the target region using labeled nucleotides. In some embodiments, the labeled nucleotides used in step (b) comprise non-terminating labeled nucleotides. In some embodiments, the unlabeled nucleotides used in step (c) comprise non-terminating unlabeled nucleotides. In some embodiments, the labeled nucleotides used in step (d) comprise non-terminating labeled nucleotides. In some embodiments, the labeled nucleotides used in step (b) or step (d) are mixed with unlabeled nucleotides of the same base. In some embodiments, 50% or fewer of the nucleotides used in step (b) or step (d) are labeled. In some embodiments, 0.1% or fewer of the nucleotides used in step (c) are labeled. In some embodiments, all of the nucleotides used in step (c) are unlabeled. In some embodiments, the method further comprises repeating step (c) one or more times until the primer is extended to the end of the homopolymer region, wherein unincorporated nucleotides are removed prior to repeating step (c). In some embodiments, different bases of the labeled nucleotides used to determine the target region are discretely used. In some embodiments, different bases of the labeled nucleotides used to determine the target region are discretely used. In some embodiments, the target region of each polynucleotide is associated with a unique barcode region.

In some embodiments, a method of determining a sequence of a region of interest from an mRNA molecule, comprises: (a) hybridizing a plurality of polynucleotides derived from mRNA with a first primer to form a first plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides; (c) hybridizing the plurality of polynucleotides with a second primer to form a second plurality of hybridized templates, wherein the second primer comprises a homopolymer region comprising a plurality of contiguous and identical bases complementary to the bases in the homopolymer region of the polynucleotides; and (d) determining the sequence of the target region using labeled nucleotides. In some embodiments, the labeled nucleotides used in step (b) comprise non-terminating labeled nucleotides. In some embodiments, the labeled nucleotides used in step (d) comprise non-terminating labeled nucleotides. In some embodiments, the labeled nucleotides used in step (b) or step (d) are mixed with unlabeled nucleotides of the same base. In some embodiments, step (c) and step (d) are performed before step (a) and step (b). In some embodiments, step (a) and step (b) are performed before step (c) and step (d). In some embodiments, the method comprises removing the first primer after step (b) or the second primer after step (d). In some embodiments, the second primer comprises a 3' anchor at the 3' end of the primer, the 3' anchor comprising a base other than the base present in the homopolymer region of the second primer. In some embodiments, the second primer comprises a 5' anchor at the 5' end of the primer, wherein the anchor is covalently bound to the homopolymer region of the second primer through a linker. In some embodiments, the 5' anchor comprises a nucleic acid segment comprising a sequence identical to at least a portion of the first primer. In some embodiments, the linker comprises one or more nucleic acids. In some embodiments, the linker is a PEG phosphoramedite linker. In some embodiments, the method further comprises extending the second primer within the homopolymer region using nucleotides. In some embodiments, the nucleotides used to extend the second primer within the homopolymer region comprise non-terminating nucleotides. In some embodiments, the nucleotides used to extend the second primer within the homopolymer region comprise unlabeled nucleotides. In some embodiments, the sequence of the target region or the barcode region is determined using a mixture of unlabeled nucleotides and the labeled nucleotides. In some embodiments, different bases of the labeled nucleotides used to determine the target region are discretely used. In some embodiments, different bases of the labeled nucleotides used to determine the target region are discretely used. In some embodiments, the target region of each polynucleotide is associated with a unique barcode region.

In some embodiments, a method of determining a sequence of a region of interest from an mRNA molecule comprises: (a) hybridizing a plurality of polynucleotides derived from mRNA with a primer to form a plurality of hybridized templates; polynucleotides comprising a barcode region, a homopolymer region comprising a plurality of contiguous and identical bases, and a target region comprising a sequence associated with a region of interest from an mRNA molecule; wherein the primer comprises a first primer segment, a second primer segment comprising a homopolymer region comprising a plurality of bases complementary to the bases in the homopolymer region of the polynucleotides, and a cleavable linker between the first primer segment and the second primer segment; (b) determining the sequence of the target region using labeled nucleotides; (c) cleaving the primer at the cleavable linker; and (d) determining the sequence of the barcode region using labeled nucleotides. In some embodiments, the labeled nucleotides used to determine the sequence of the target region in step (b) comprise non-terminating labeled nucleotides. In some embodiments, the labeled nucleotides used to determine the sequence of the barcode region in step (d) comprise non-terminating labeled nucleotides. In some embodiments, the labeled nucleotides used in step (b) or step (d) are mixed with unlabeled nucleotides of the same base. In some embodiments, the cleavable linker comprises one or more nucleic acids. In some embodiments, the cleavable linker comprises a uracil base, and wherein the primer is cleaved by contacting the primer with a uracil-specific cleaving enzyme. In some embodiments, the method further comprises extending the second primer segment within the homopolymer region using nucleotides. In some embodiments, the nucleotides used to extend the second primer segment within the homopolymer region comprise non-terminating nucleotides. In some embodiments, the nucleotides used to extend the second primer segment within the homopolymer region comprise unlabeled nucleotides. In some embodiments, the sequence of the target region or the barcode region is determined using a mixture of unlabeled nucleotides and the labeled nucleotides. In some embodiments, different bases of the labeled nucleotides used to determine the target region are discretely used. In some embodiments, different bases of the labeled nucleotides used to determine the target region are discretely used. In some embodiments, the target region of each polynucleotide is associated with a unique barcode region.

In some embodiments, a method of determining a sequence of a region of interest from an mRNA molecule comprises: (a) hybridizing a plurality of polynucleotide derived from mRNA with a primer to form a plurality of hybridized templates, wherein the polynucleotides comprise a homopolymer region comprising a plurality of contiguous and identical bases and a target region comprising a sequence associated with a region of interest from an mRNA molecule; (b) extending the primer into the homopolymer region using nucleotides of the same base, wherein the primer stalls within the homopolymer region, and removing unincorporated nucleotides; (c) repeating step (b) one or more times to extend the primer through the homopolymer region; and (d) determining the sequence of the target region using labeled nucleotides. In some embodiments, the nucleotides used to extend the primer in step (b) comprise non-terminating labeled nucleotides. In some embodiments, the labeled nucleotides used to determine the sequence of the target region in step (d) comprise non-terminating labeled nucleotides. In some embodiments, the nucleotides used in step (b) comprise labeled nucleotides. In some embodiments, the nucleotides used in step (b) comprise unlabeled nucleotides. In some embodiments, the sequence of the target region is determined using a mixture of unlabeled nucleotides and the labeled nucleotides. In some embodiments, the polynucleotides further comprise a barcode region, and wherein the target region is associated with a unique barcode region, the method further comprising determining the sequence of the barcode region using labeled nucleotides.

In some embodiments of any of the above methods, the bases in the homopolymer region of the polynucleotides are adenine or thymine bases.

In some embodiments of any of the above methods, the homopolymer region of the polynucleotides comprises as least 8 contiguous and identical bases. In some embodiments, the homopolymer region of the polynucleotides comprises as least 50 contiguous and identical bases.

In some embodiments of any of the above methods, the barcode region comprises a sample barcode.

In some embodiments of any of the above methods, the method further comprises associating the determined sequence of the barcode region with the determined sequence associated with the mRNA coding region from the same target nucleic acid molecule.

In some embodiments of any of the above methods, the polynucleotides are cDNA molecules.

In some embodiments of any of the above methods, the region of interest of the mRNA molecule comprises a coding region of the mRNA molecule.

In some embodiments of any of the above methods, the region of interest of the mRNA molecule comprises a 3'-untranslated region or a 5'-untranslated region of the mRNA molecule.

DETAILED DESCRIPTION OF THE INVENTION

Figure 1:
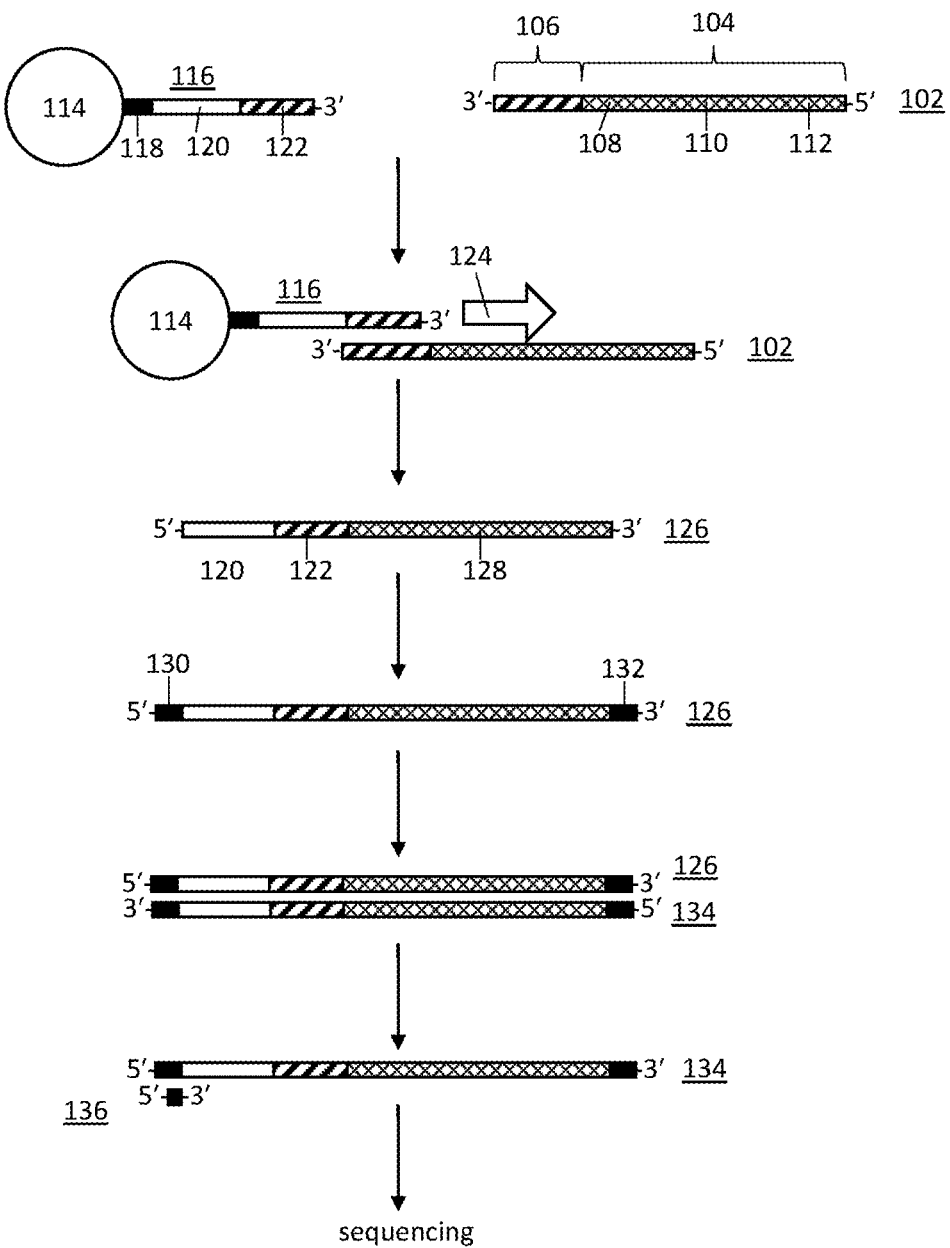
FIG. 1 illustrates an exemplary method for obtaining polynucleotides that can be sequenced using the methods described herein.

Described herein are methods of determining a sequence of a region of interest within an mRNA molecule (e.g., a coding region, a 3' untranslated region (3'-UTR), and/or a 5' untranslated region (5'-UTR)). The methods allow for sequencing the region of interest within the mRNA molecule while avoiding sequencing all or substantial portions of the homopolymer region (e.g., the poly-A region or its complement, a poly-T region). The poly-A region of an mRNA molecule is generally considered uninteresting and uninformative, as it does not provide significant information about the mRNA sequence or gene expression levels. Therefore, there is substantial benefit in reducing the cost or time required to extend the sequencing primer through the homopolymer region to reach a more informative region of the polynucleotide. For example, cost can be reduced by extending the sequencing primer while reducing or eliminating the use of labeled nucleotides, which are substantially more expensive than non-labeled nucleotide counterparts. Further, sequencing primer extension time can be reduced by skipping the detection step for each incorporated base, and allowing the primer to continuously extend through the homopolymer region.

Sequenced polynucleotides may include a barcode region, which can include, for example, a sample barcode and/or a unique molecular identifier (UMI). The homopolymer region can be positioned in the polynucleotide between the barcode region and the region of interest in the mRNA molecule. This results in a situation where two regions for which knowledge of the sequence is desired (i.e., the barcode region and the region of interest from the mRNA molecule) are separated by an uninteresting region (the homopolymer region). Some of the methods described herein allow for sequencing both the barcode region and the mRNA region of interest, while minimizing the disruption caused by the presence of the homopolymer region.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, wherein the barcode region omits the same base present in the homopolymer region; (b) determining the sequence of the barcode region using labeled nucleotides that lack a complement base of the same base present in the homopolymer region; (c) extending the primer within the homopolymer region using nucleotides complementary to the base present in the homopolymer region; and (d) determining the sequence of the target region using labeled nucleotides. Optionally, the nucleotides are non-terminating nucleotides.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides and unlabeled nucleotides at a first proportion of labeled nucleotides to total nucleotides; (c) extending the primer using labeled nucleotides complementary to the base present in the homopolymer region at a second proportion of labeled nucleotides to total nucleotides, wherein the second proportion of is greater than the first proportion, and wherein primer extension stalls within the homopolymer region; (d) extending the primer to the end of the homopolymer region using unlabeled nucleotides complementary to the base present in the homopolymer region; and (e) determining the sequence of the target region using labeled nucleotides. Optionally, the nucleotides are non-terminating nucleotides.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, and wherein the target region is associated with a unique barcode region; (b) determining the sequence of the barcode region using labeled nucleotides in a plurality of predetermined cycles, wherein the predetermined cycles and the barcode regions of the polynucleotides are configured such that the primer is extended to the end of the barcode region across the plurality of polynucleotides before being extended into the homopolymer region; (c) extending the primer within the homopolymer region using unlabeled nucleotides; and (d) determining the sequence of the target region using labeled nucleotides. Optionally, the nucleotides are non-terminating nucleotides.

In some embodiments, there is a method of determining a sequence of a region of interest from an mRNA molecule, comprising: (a) hybridizing a plurality of polynucleotides derived from mRNA with a first primer to form a first plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides; (c) hybridizing the plurality of polynucleotides with a second primer to form a second plurality of hybridized templates, wherein the second primer comprises a homopolymer region comprising a plurality of contiguous and identical bases complementary to the bases in the homopolymer region of the polynucleotides; and (d) determining the sequence of the target region using labeled nucleotides. Optionally, the nucleotides are non-terminating nucl eoti des.

In some embodiments, there is a method of determining a sequence of a region of interest from an mRNA molecule, comprising: (a) hybridizing a plurality of polynucleotides derived from mRNA with a primer to form a plurality of hybridized templates; polynucleotides comprising a barcode region, a homopolymer region comprising a plurality of contiguous and identical bases, and a target region comprising a sequence associated with a region of interest from an mRNA molecule; wherein the primer comprises a first primer segment, a second primer segment comprising a homopolymer region comprising a plurality of bases complementary to the bases in the homopolymer region of the polynucleotides, and a cleavable linker between the first primer segment and the second primer segment; (b) determining the sequence of the target region using labeled nucleotides; (c) cleaving the primer at the cleavable linker; and (d) determining the sequence of the barcode region using labeled nucleotides. Optionally, the nucleotides are non-terminating nucleotides.

In some embodiments, there is a method of determining a sequence of a region of interest from an mRNA molecule, comprising: (a) hybridizing a plurality of polynucleotide derived from mRNA with a primer to form a plurality of hybridized templates, wherein the polynucleotides comprise a homopolymer region comprising a plurality of contiguous and identical bases and a target region comprising a sequence associated with a region of interest from an mRNA molecule; (b) extending the primer into the homopolymer region using nucleotides of the same base, wherein the primer stalls within the homopolymer region, and removing unincorporated nucleotides; (c) repeating step (b) one or more times to extend the primer through the homopolymer region; and (d) determining the sequence of the target region using labeled nucleotides. Optionally, the nucleotides are non-terminating nucleotides.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The terms "individual," "patient," and "subject" are used synonymously, and refers to an animal including a human.

The term "label," as used herein, refers to a detectable moiety that is coupled to or may be coupled to another moiety, for example, a nucleotide or nucleotide analog. The label can emit a signal or alter a signal delivered to the label so that the presence or absence of the label can be detected. In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase, or protease).

A "non-terminating nucleotide" is a nucleic acid moiety that can be attached to a 3' end of a polynucleotide using a polymerase or transcriptase, and that can have another non-terminating nucleic acid attached to it using a polymerase or transcriptase without the need to remove a protecting group or reversible terminator from the nucleotide. Naturally occurring nucleic acids are a type of non-terminating nucleic acid. Non-terminating nucleic acids may be labeled or unlabeled.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

FIGS. 1-8 illustrate processes according to various embodiments. In the exemplary processes, some blocks are, optionally, combined, the order of some blocks is, optionally, changed, and some blocks are, optionally, omitted. In some examples, additional steps may be performed in combination with the exemplary processes. Accordingly, the operations as illustrated (and described in greater detail below) are exemplary by nature and, as such, should not be viewed as limiting.

The disclosures of all publications, patents, and patent applications referred to herein are each hereby incorporated by reference in their entireties. To the extent that any reference incorporated by reference conflicts with the instant disclosure, the instant disclosure shall control.

Polynucleotides

Polynucleotides used in the methods described herein can include a homopolymer region and a target region. In some embodiments, the polynucleotides further comprise a barcode region. Generally, the polynucleotides are derived from an mRNA molecule, for example by generating a complementary DNA (cDNA) molecule from a reverse transcriptase enzyme. In some embodiments, the polynucleotide is a complement of the cDNA molecule. A plurality of polynucleotides can be derived from a plurality of mRNA molecules, and the different polynucleotides can include a sequence that reflects the different mRNA molecules. As different mRNA molecules may include different sequences for the region of interest and/or different homopolymer (e.g., poly-A region) lengths, so too can the polynucleotides include different target regions and/or different homopolymer lengths.

The target region of the polynucleotide includes a sequence associated with a region of interest from an mRNA molecule. The sequence may be, for example, the same as or complementary to the region of interest from the mRNA molecule. The region of interest may include one or more a 3'-UTR, 5'-UTR, and/or a coding region, or a portion of any one of these regions, from an mRNA molecule.

The polynucleotides include a homopolymer region (e.g., a poly-A or poly-T region), which is representative of the poly-A region in the mRNA molecule, or its complement. In some embodiments, the homopolymer region of the polynucleotides is about 5 bases in length or more, about 8 bases in length or more, about 10 bases in length or more, about 20 bases in length or more, about 30 bases in length or more, about 40 bases in length or more, about 50 bases in length or more, about 100 bases in length or more, or about 200 bases in length or more. In some embodiments, the homopolymer region of the polynucleotides is about 5 bases to about 200 bases in length, such as about 5 bases to about 8 bases in length, about 8 bases to about 10 bases in length, about 10 bases to about 20 bases in length, about 20 bases to about 30 bases in length, about 30 bases to about 40 bases in length, about 40 bases to about 50 bases in length, about 50 bases to about 100 bases in length, or about 100 bases to about 200 bases in length.

In some embodiments, the polynucleotides include a barcode region (e.g., a sample barcode and/or a UMI). In some embodiments, the polynucleotides are derived from different mRNA molecules, and can therefore include different target regions of interest from the different mRNA molecules, and, if present, may include different barcode regions to uniquely identify original mRNA molecules. In some embodiments, the barcode region includes a sample barcode. The sample barcode can be unique for a given sample, and can therefore be common across the capture primers used for the same sample (e.g., from the same patient, same tissue of a patient, or from the same cell). Thus, polynucleotides from different samples can be combined for multiplexed sequencing, and the source of any given sequenced polynucleotide can be determined based on the sample barcode.

In some embodiments, the homopolymer region of the polynucleotide is positioned between the target region and the barcode region. For example, in some embodiments, the 5' end of the homopolymer region is proximal to the 3' end of the target region, and the 3' end of the homopolymer region is proximal to the 5' end of the barcode region. In some embodiments, the 3' end of the homopolymer region is proximal to the 5' end of the target region, and the 5' end of the homopolymer region is proximal to the 3' end of the barcode region. In some embodiments, there are no intervening bases between the barcode region and the homopolymer region. In some embodiments, there are no intervening bases between the homopolymer region and the target region.

mRNA can be isolated from a biological sample (e.g., a sample derived from a blood sample, cell sample, tissue sample, or other biological sample) using a capture primer (such as a DNA capture primer). For example, a blood sample can be drawn or a tissue sample biopsied to obtain the biological sample. In some embodiments, the biological sample is a single cell, and mRNA from a single cell can be labeled with a common sample barcode (e.g., single-cell RNA sequencing, or "scRNA-seq"). In some embodiments, the capture primer includes a poly-T sequence, which hybridizes to the poly-A tail at the 3' end of the mRNA. The capture primer may be bound to a surface, such as a bead or other attachment surface, and unbound nucleic acid molecules or other biological debris can be removed. In some embodiments, the capture primer can include a barcode region. The barcode region may include a unique molecular identifier (UMI), which becomes associated with the mRNA molecule hybridized to that particular capture primer. Thus, a plurality of different mRNA molecules can be capture with unique barcode regions.

The capture primer hybridized to an mRNA molecule can be extended using a reverse transcriptase to generate a cDNA molecule. The cDNA molecule includes the poly-T homopolymer region, along with the barcode region of the capture primer, if the barcode is to be present in the final polynucleotide. In some embodiments, a complement of the cDNA molecule is generated, and the cDNA molecule and/or the complement of the cDNA molecule are used as a template for sequencing. In some embodiments, the poly-T homopolymer region in the capture probe is about 5 bases in length to about 50 bases in length, such as about 10 to about 30 bases in length, or about 20 bases in length.

FIG. 1 illustrates an exemplary method for obtaining polynucleotides that can be sequenced using the methods described herein. mRNA molecules 102 include a target region 104 and a poly-A homopolymer region 106 proximal to the 3' end of the target region 102. The target region can include a 3'-UTR 108, a coding region 110, and a 5'-UTR. The mRNA molecules 102 obtained from a sample can be hybridized to a capture probe 116, which is generally fused to a surface 114 such as a bead or other suitable surface. The capture probe 116 includes a joining region 118 that attaches the capture probe 116 to the surface 114, a barcode region 120 (optional), and a poly-T homopolymer region 122. The poly-T homopolymer region 122 of the capture probe hybridizes to the poly-A homopolymer region 106 of the mRNA molecule. The surface 114, including the attached capture probe 116 hybridized to the mRNA molecule 102 may be washed to remove uncaptured polynucleotides or other material from the sample. A reverse transcriptase 124 to extend the capture probe 116, using the mRNA molecule 102 as a template. This generates a cDNA molecule 126, which includes a target region 128 complementary to the target region of the mRNA molecule 102, a poly T homopolymer region 122 and a barcode region 120. The joining region 118 can be cleaved from the surface 114, thereby releasing the cDNA molecule 126. Adapters 130 and 132 may be ligated to the 3' and/or 5' end of the cDNA molecule 126. A complement 134 of the cDNA molecule 126 can be generated, which can be hybridized to a sequencing primer 136 to generate a hybridized template. In either embodiment, the hybridized template may proceed to any of the sequencing methods described herein.

Flow Sequencing Methods

Using the methods described herein, the sequence of a region of interest from an mRNA molecule can be determined. The polynucleotides derived from the mRNA are hybridized to a sequencing primer to generate the hybridization templates for sequencing. The methods described herein can include sequencing polynucleotides using flow sequencing methods, which may also be referred to as "natural sequencing-by-synthesis," or "non-terminated sequencing-by-synthesis" methods. Exemplary methods are described in U.S. Pat. No. 8,772,473, which is incorporated herein by reference in its entirety. While the following description is provided in reference to flow sequencing methods, it is understood that other sequencing methods may be used to sequence all or portion (e.g., one or more regions, such as the barcode region and/or the target region). Flow sequencing includes the use of nucleotides to extend a primer hybridized to a polynucleotide. Nucleotides of a given base type (e.g., A, C, G, T, U, etc.) can be mixed with hybridized templates to extend the primer if a complementary base is present in the template strand. The nucleotides may be, for example, non-terminating nucleotides. When the nucleotides are non-terminating, more than one consecutive base can be incorporated into the extending primer strand if more than one consecutive complementary base is present in the template strand. The non-terminating nucleotides contrast with nucleotides having 3' reversible terminators, wherein a blocking group is generally removed before a successive nucleotide is attached. If no complementary base is present in the template strand, primer extension ceases until a nucleotide that is complementary to the next base in the template strand is introduced. At least a portion of the nucleotides can be labeled so that incorporation can be detected. Most commonly, only a single nucleotide type is introduced at a time (i.e., discretely added), although two or three different types of nucleotides may be simultaneously introduced in certain embodiments. This methodology can be contrasted with sequencing methods that use a reversible terminator, wherein primer extension is stopped after extension of every single base before the terminator is reversed to allow incorporation of the next succeeding base.

The nucleotides can be introduced at a determined order, which may be further divided into cycles. Nucleotides are added stepwise, which allows incorporation of the added nucleotide to the end of the sequencing primer if a complementary base in the template strand is present. The cycles may have the same order of nucleotides and number of different base types (i.e., symmetrical cycles) or a different order of nucleotides and/or a different number of different base types (i.e., asymmetrical cycles). However, no base is repeated in the same cycle, which provides a marker to distinguish between different cycles. Solely by way of example, the order of a first cycle may be A-T-G-C and the order of a second cycle may be A-T-C-G. Further, one or more cycles may omit one or more nucleotides. Solely by way of example, the order of a first cycle may be A-T-G-C and the order of a second cycle may be A-T-C. Alternative orders may be readily contemplated by one skilled in the art. Between the introductions of different nucleotides, unincorporated nucleotides may be removed, for example by washing the sequencing platform with a wash fluid.

A polymerase can be used to extend a sequencing primer by incorporating one or more nucleotides at the end of the primer in a template-dependent manner. In some embodiments, the polymerase is a DNA polymerase. In some embodiments, the polymerase is an RNA polymerase. The polymerase may be a naturally occurring polymerase or a synthetic (e.g., mutant) polymerase. The polymerase can be added at an initial step of primer extension, although supplemental polymerase may optionally be added during sequencing, for example with the stepwise addition of nucleotides or after a number of flow cycles.

The presence or absence of an incorporated labeled nucleic acid can be detected to determine a sequence. The label may be, for example, an optically active label (e.g., a fluorescent label) or a radioactive label, and a signal emitted by or altered by the label can be detected using a detector.

A flowgram can be generated based on the detection of an incorporated nucleotide and the order of nucleotide introduction. Take, for example, the flowing template sequences: CTG and CAG, and a repeating flow cycle of T-A-C-G. A resulting flowgram is shown in Table 1, where 1 indicates incorporation of an introduced nucleotide and 0 indicates no incorporation of an introduced nucleotide. The flowgram can be used to determine the sequence of the template strand.

TABLE 1

| Sequence | Cycle 1 | | | | Cycle 2 | | | |
|---|---|---|---|---|---|---|---|---|
| | T | A | C | G | T | A | C | G |
| CTG | 0 | 0 | 0 | 1 | 0 | 1 | 1 | 0 |
| CAG | 0 | 0 | 0 | 1 | 1 | 0 | 1 | 0 |

The introduced nucleotides can include labeled nucleotides when determining the sequence of the template strand. The label may be, for example, a fluorescent label. The presence or absence of a labeled nucleotide incorporated into a primer hybridized to a template polynucleotide can be detected, which allows for the determination of the sequence (for example, by generating a flowgram). In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. For example, the label may be cleaved after detection and before incorporation of the successive nucleotide(s). In some embodiments, the label (or linker) is attached to the nucleotide base, or to another site on the nucleotide that does not interfere with elongation of the nascent strand of DNA. In some embodiments, the linker comprises a disulfide or PEG-containing moiety.

In some embodiment, the nucleotides introduced include only unlabeled nucleotides, and in some embodiments the nucleotides include a mixture of labeled and unlabeled nucleotides. For example, in some embodiments, the portion of labeled nucleotides compared to total nucleotides is about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.02.5% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

Prior to sequencing, the polynucleotides can be hybridized to primers fixed to a solid support. The primers may hybridize to adapter regions on the 3' and/or 5' ends of the polynucleotides. The polynucleotides may be amplified (for example, by bridge amplification or other amplification techniques) after hybridization to generate polynucleotide sequencing colonies. Colony formation allows for signal amplification so that the detector can accurately detect incorporation of labeled nucleotides for each colony.

Additional methods for sequencing and/or analyzing sequencing data that may be used in accordance with the methods described herein is described in U.S. Patent Application Ser. No. 16/864,971; U.S. Patent Application Ser. No. 16/864,981; and International PCT Application No. PCT/US2020/031196; the contents of each of which are incorporated herein by reference.

Controlled Primer Extension Through Barcode Region Design

The barcode regions are artificial constructs that are used to label individual mRNA molecules from the biological sample. As such, in some embodiments, the barcode regions are designed to omit the same base present in the homopolymer region. The barcode region is sequenced, for example using a flow sequencing method, which allows the sequencing primer to extend through the barcode region. However, since the barcode region does not include the base present in the homopolymer region (e.g., an adenine or thymine base), the base complementary to the base of the homopolymer region can be omitted form the flow sequencing cycle order while the barcode region is being sequenced and the primer extended within the barcode region. Once the primer is extended to the start of the homopolymer region, the primer can be extended using nucleotides (such as non-terminating nucleotides) complementary to the base present in the homopolymer region to extend the primer within the homopolymer region. The nucleotides used to extend the primer within the homopolymer region may be unlabeled, labeled, or a mixture of labeled and unlabeled nucleotides (such as non-terminating unlabeled nucleotides). In some embodiments, the nucleotides used to extend the primer within the homopolymer region comprise unlabeled nucleotides, such as non-terminating unlabeled nucleotides. In some embodiments, the nucleotides used to extend the primer within the homopolymer region comprise unlabeled nucleotides and labeled nucleotides (such as unlabeled non-terminating nucleotides and labeled non-terminating nucleotides), wherein the proportion of labeled nucleotides compared to total nucleotides used to extend the primer within the homopolymer region of the polynucleotide is less than the proportion used to extend the primer within the barcode region and/or the target region of the polynucleotide.

In some embodiments, the homopolymer region is a poly-A region, and the barcode regions omit adenine bases. In some embodiments, the homopolymer region is a poly-T region, and the barcode regions omit thymine bases.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, wherein the barcode region omits the same base present in the homopolymer region; (b) determining the sequence of the barcode region using labeled nucleotides that lack a complement base of the same base present in the homopolymer region; (c) extending the primer within the homopolymer region using nucleotides complementary to the base present in the homopolymer region; and (d) determining the sequence of the target region using labeled nucleotides.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, wherein the barcode region omits the same base present in the homopolymer region; (b) determining the sequence of the barcode region using labeled non-terminating nucleotides that lack a complement base of the same base present in the homopolymer region; (c) extending the primer within the homopolymer region using non-terminating nucleotides complementary to the base present in the homopolymer region; and (d) determining the sequence of the target region using labeled non-terminating nucleotides.

Sequencing primers are hybridized to a plurality of polynucleotides derived from mRNA to form a plurality of hybridized templates. The polynucleotides can include an adapter region on the 3' and/or 5' end of the polynucleotide, and the adapter region can hybridize to the sequencing primer.

Once the hybridized templates are formed the primer can be extended through the barcode region, for example using a flow sequencing method. During sequencing of the barcode region, the primer is extended by contacting the hybridized templates with the nucleotides (comprising labeled nucleotides, and optionally unlabeled nucleotides) in a defined order. However, the defined order omits the complement base of the same base present in the homopolymer region while the primer is extended within the barcode region. Nucleotide types (e.g., A, C, G, or T, except the base complementary to the base in the homopolymer region) may be discretely contacted with the hybridized template. That is, the nucleotides are added one at a time in a predetermined order. In some embodiments, two or three different nucleotide types are simultaneously used. A DNA polymerase can be used to incorporate the nucleotide onto the 3' end of the primer in a template-dependent manner, thereby extending the primer. Template-dependent extension of the primer occurs if a complementary base (that is, complementary to the added nucleotide) is present in the template polynucleotide strand at a position opposite the position of the newly incorporated base. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined, wherein the complement base of the same base present in the homopolymer region is omitted from the order. In this manner, the primer is extended through the barcode region, but does not extend into the homopolymer region. Thus, primer extension stalls prior to the start of the homopolymer region until a base complementary to the homopolymer region is introduced.

Because the sequence of the homopolymer region is generally uninteresting, the primer can be extended within the homopolymer region without detecting the presence or absence of nucleotide incorporation, for example by using unlabeled nucleotides or not detecting the label (e.g., fluoresce). Labeled nucleotides are generally more expensive and have an increased risk of the primer extension stalling, so the labeled nucleotides may be included as a smaller proportion of the total nucleotides (compared to the portion used to determine the sequence of the barcode region) or eliminated during the primer extension through the homopolymer region. In the event primer extension stalls within the homopolymer region, unincorporated nucleotides can be removed, for example by washing the hybridized templates, and fresh nucleotides complementary to the base present in the homopolymer region can be added.

In some embodiments, the primer is extended within the homopolymer region using unlabeled nucleotides. In some embodiments, the primer is extended within the homopolymer region using labeled nucleotides. In some embodiments, the primer is extended within the homopolymer region using both labeled nucleotides and unlabeled nucleotides. For example, in some embodiments, the portion of labeled nucleotides compared to total nucleotides is about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

In contrast to sequencing the barcode region, sequencing the targeting region can includes an ordered use of all four bases (A, T, G, C) without omitting the base present in the homopolymer region, as the all four bases may be present in the target region. A polymerase can be used to incorporate the nucleotide onto the 3' end of the primer in a template-dependent manner, thereby extending the primer from the end of the homopolymer region and into the target region. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Figure 2A:
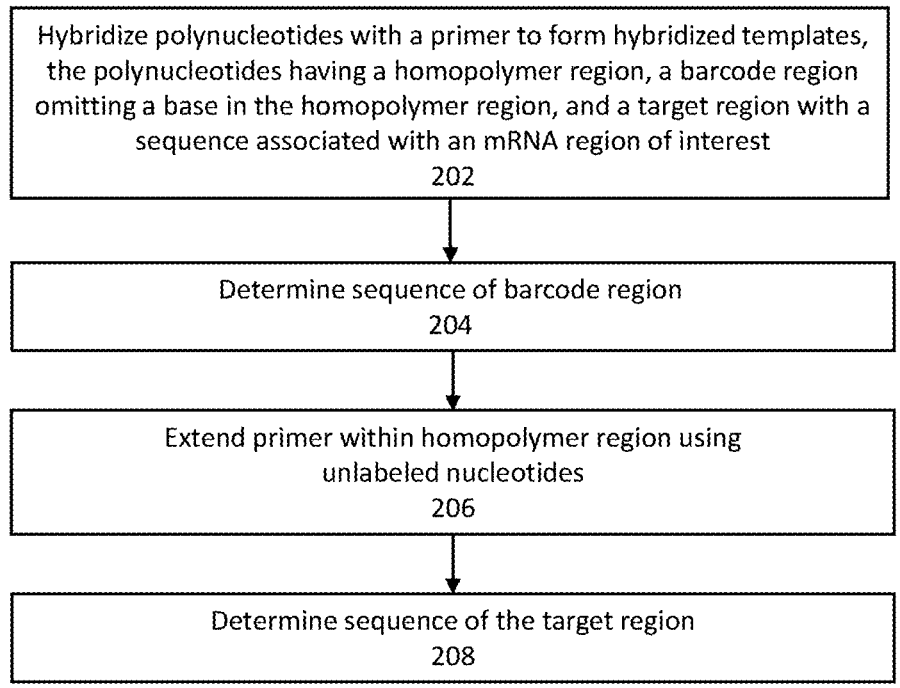
FIG. 2A shows an flow chart of an exemplary method for determining a sequence of a region of interest from an mRNA molecule, wherein the barcode region omits the same base present in the homopolymer region.
Figure 2B:
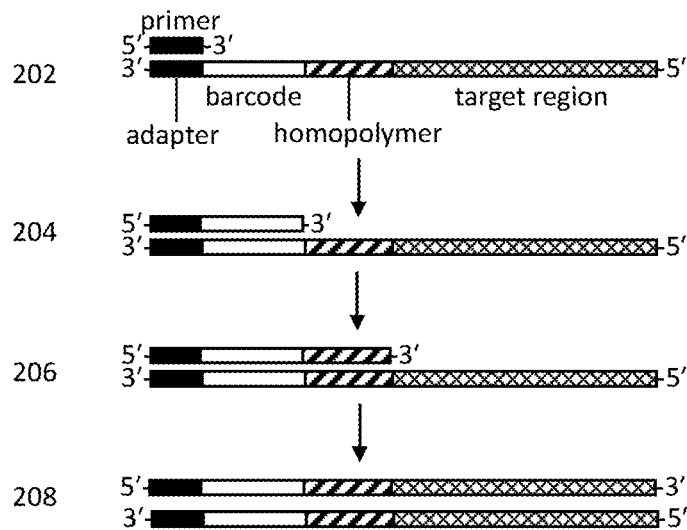
FIG. 2B shows an exemplary method for determining a sequence of a region of interest from an mRNA molecule, wherein the barcode region omits the same base present in the homopolymer region, in graphical form.

FIG. 2A shows an flow chart of an exemplary method for determining a sequence of a region of interest from an mRNA molecule, wherein the barcode region omits the same base present in the homopolymer region. FIG. 2B shows an exemplary method in graphical form. At step 202, polynucleotides having a homopolymer region, a barcode region, and a target region comprising a sequence associated with (e.g., complementary to or identical to) an mRNA region of interest are hybridized to a primer to form hybridized templates. The different polynucleotides contain different barcode regions and different target regions such that the different target regions across the polynucleotides are associated with a unique molecular identifier. The 3' end of the polynucleotide can include an adapter region, and the primer can hybridize to the adapter region of the polynucleotide. The adapter region is proximal to the 3' end of the barcode region. As shown in FIG. 2B, the homopolymer region is positioned between the target region and the barcode region, with the barcode region proximal to the 3' end of the homopolymer region. The barcode regions, however, omit the same base present in the homopolymer region. For example, if the homopolymer region is a poly-A sequence, the different barcodes contain different sequences of T, C, and/or G, but omit A. Similarly, if the homopolymer region is a poly-T sequence, the different barcodes contain different sequences of A, C, and/or G. The polynucleotide may further include an adapter region, and the primer hybridizes to the adapter region. Thus, during primer extension, the polynucleotide functions as a template strand from the extension of the primer strand.

At step 204 of FIG. 2A and FIG. 2B, the sequence of the barcode region is determined using nucleotides that lack a complement base of the same base present in the homopolymer region. For example, the barcode region may be sequenced using a flow sequencing method. At least a portion of the nucleotides are labeled. In some embodiments, the nucleotides comprise labeled nucleotides and unlabeled nucleotides.

At step 206 of FIG. 2A and FIG. 2B, the primer is extended within the homopolymer region using nucleotides complementary to the base present in the homopolymer region. The nucleotides may be labeled, unlabeled, or a mixture of both labeled and unlabeled nucleotides. In some embodiments, the presence or absence of nucleotide incorporation during primer extension within the homopolymer region is not detected.

Once the primer has been extended through the homopolymer region, the sequence of the target region is determined using nucleotides, as shown in step 208 in FIG. 2A and FIG. 2B, for example using a flow sequencing method. At least a portion of the nucleotides are labeled during sequencing. In some embodiments, the nucleotides comprise labeled nucleotides and unlabeled nucleotides. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Primer Extension Stalling Within Homopolymer Region

In some embodiments of a method of determining a sequence of a region of interest from an mRNA molecule, primer extension within the homopolymer region is stalled by using a higher proportion of labeled nucleotides compared to the proportion of labeled nucleotides used when determining the sequence of other regions of the polynucleotide (e.g., the barcode region and/or the target region). The nucleotides used to extend to the primer can include labeled nucleotides or a mixture of labeled and unlabeled nucleotides. As the proportion of labeled nucleotides relative to the total amount of nucleotides (i.e., the sum of labeled and non-labeled nucleotides) increases, the likelihood that the polymerase used to extend the primer will stall increases. Thus, primer extension can be intentionally stalled within the homopolymer region using a higher proportion of labeled nucleotides, unincorporated nucleotides can be removed, and primer extension can be continued using unlabeled nucleotides.

For example, a method of determining a sequence of a region of interest from an mRNA molecule can include: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides and unlabeled nucleotides at a first proportion of labeled nucleotides to total nucleotides; (c) extending the primer using labeled nucleotides complementary to the base present in the homopolymer region at a second proportion of labeled nucleotides to total nucleotides, wherein the second proportion of is greater than the first proportion, and wherein primer extension stalls within the homopolymer region; (d) extending the primer to the end of the homopolymer region using unlabeled nucleotides complementary to the base present in the homopolymer region; and (e) determining the sequence of the target region using labeled nucleotides.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled non-terminating nucleotides and unlabeled non-terminating nucleotides at a first proportion of labeled non-terminating nucleotides to total non-terminating nucleotides; (c) extending the primer using labeled non-terminating nucleotides complementary to the base present in the homopolymer region at a second proportion of labeled non-terminating nucleotides to total non-terminating nucleotides, wherein the second proportion of is greater than the first proportion, and wherein primer extension stalls within the homopolymer region; (d) extending the primer to the end of the homopolymer region using unlabeled non-terminating nucleotides complementary to the base present in the homopolymer region; and (e) determining the sequence of the target region using labeled non-terminating nucleotides.

In some embodiments, the barcode region is proximal to the 3' end of the homopolymer region. In some embodiments, there are no intervening bases between the barcode region and the homopolymer region. The primer can then be extended through the barcode region, and optionally into the homopolymer region before the proportion of labeled nucleotides is increased.

Once the hybridized templates are formed, the primer can be extended through the barcode region, for example using a flow sequencing method. During sequencing of the barcode region, the primer is extended by contacting the hybridized templates with the nucleotides (comprising labeled nucleotides and, optionally, unlabeled nucleotides) in a defined order. Nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined.

Once the primer is extended to the homopolymer region, the proportion of labeled nucleotides used to extend the primer can be increased to intentionally stall primer extension. Because an increase proportion of labeled nucleotides to total nucleotides increases the likelihood that the polymerase will stall, the proportion of labeled nucleotides to total nucleotides is higher when stalling primer extension within the homopolymer region than the proportion of labeled nucleotides used to determine the sequence of the barcode region and the targeting region. That is, the proportion of labeled nucleotides to total nucleotides used to determine the sequences of the barcodes region is lower than the proportion of labeled nucleotides to total nucleotides used to extend the primer within the homopolymer region so that the primer extension stalls within the homopolymer region.

The probability that the polymerase stalls depends on the type of polymerase, the structure of the labeled nucleotide (e.g., the structure of the label or the linker between the label and the nucleotide), and the proportion of labeled nucleotides to total nucleotides used during primer extension. Stalling of the polymerase during sequence determination (e.g., when determining the sequence of the barcode region or target region) is generally undesirable. However, because the sequence of the homopolymer region is generally unimportant, in some embodiments, the polymerase is stalled intentionally. Thus, the proportion of labeled nucleotides used to extend the primer within the homopolymer region, thereby stalling the primer extension within the polymer region, is generally greater than the proportion of labeled nucleotides used when determining a sequence (such as the sequence of the barcode region and/or target region). The proportion of labeled nucleotides used to induce or limit stalling of the primer extension can be readily selected by one of skill in the art. For example, in some embodiments, the portion of labeled nucleotides compared to total nucleotides is about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 50 to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

After primer extension stalls within the homopolymer region, extension can be restarted using unlabeled nucleotides complementary to the base present in the homopolymer region. Optionally, both labeled and unlabeled nucleotides can be used, although the proportion of labeled nucleotides used to continue primer extension within the homopolymer region after stalling the primer extension should be lower than the proportion used when stalling the primer extension, and may further be lower than the proportion used when determining a sequence of a region (e.g., the barcode region and/or the target region). In some embodiments, labeled nucleotides are not used when extending the primer within the homopolymer region after stalling the primer within the homopolymer region. In some embodiments, less than about 5%, less than about 4%, less than about 3%, less than about 2%, less than about 1%, less than about 1%, less than about 0.5%, less than about 0.1%, less than about 0.05%, or less than about 0.01% of the total nucleotides used to continue extension of the primer within the homopolymer region after the primer extension has stalled are labeled nucleotides.

Although the probability of primer extension stall is reduced by reducing or eliminating the proportion of labeled nucleotides, primer extension may still stall within the homopolymer region after reducing the proportion of labeled nucleotides relative to the proportion included when the primer extension was intentionally stalled. To re-start primer extension after stalling, unincorporated nucleotides and the polymerase can be removed (for example, by washing the hybridized templates), and then again contacting the hybridized templates with fresh, unlabeled nucleotides and polymerase. This process may be repeated 1, 2, 3, 4, or more times until the primer is extended through the homopolymer region.

The primer can be extended to the end of homopolymer region using the unlabeled nucleotides (or the small proportion of labeled nucleotides) to the target region. As the target region includes the sequence associated with the mRNA region of interest, sequencing is restarted once the primer extends to the target region, for example using a flow sequencing method. A polymerase can be used to incorporate labeled nucleotide onto the 3' end of the primer in a template-dependent manner, thereby extending the primer from the end of the homopolymer region and into the target region. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Figure 3A:
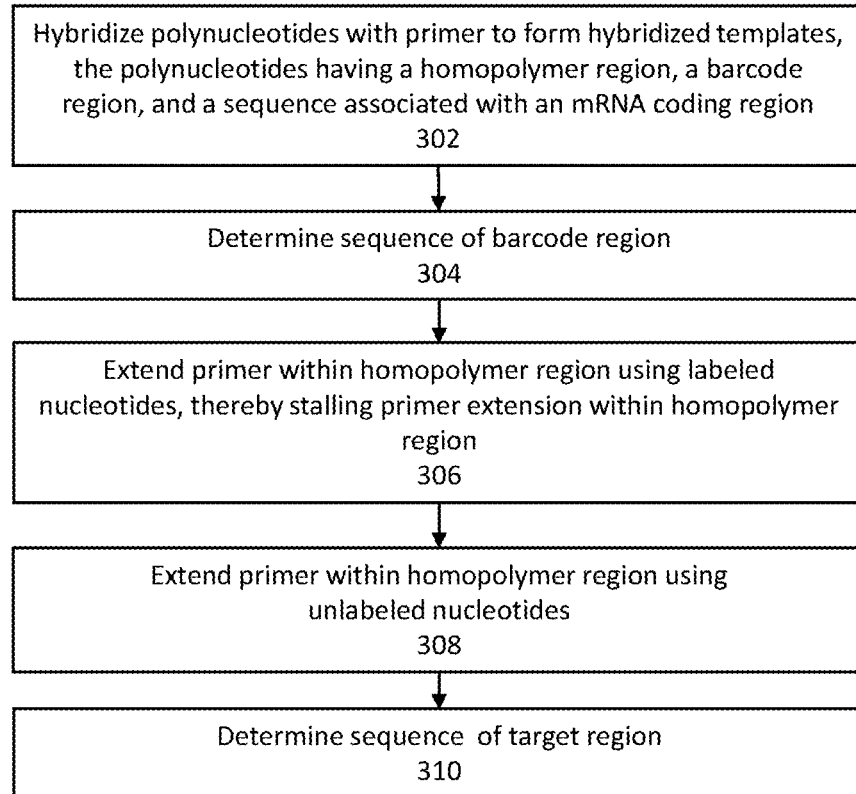
FIG. 3A shows an flow chart of an exemplary method for determining a sequence of a region of interest from an mRNA molecule, wherein primer extension is stalled within the homopolymer region.
Figure 3B:
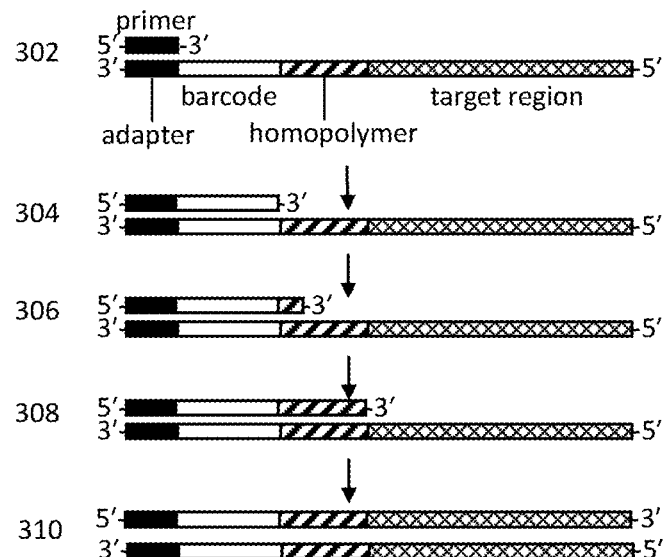
FIG. 3B shows an exemplary method for determining a sequence of a region of interest from an mRNA molecule, wherein primer extension is stalled within the homopolymer region, in graphical form.

FIG. 3A shows an flow chart of an exemplary method for determining a sequence of a region of interest from an mRNA molecule, wherein primer extension is stalled within the homopolymer region. FIG. 3B shows an exemplary method in graphical form. At step 302, polynucleotides having a homopolymer region, a barcode region, and a target region comprising a sequence associated with (e.g., complementary to or identical to) an mRNA region of interest are hybridized to a primer to form hybridized templates. The different polynucleotides contain different barcode regions and different target regions such that the different target regions across the polynucleotides are associated with a unique molecular identifier. The 3' end of the polynucleotide can include an adapter region, and the primer can hybridize to the adapter region of the polynucleotide. The adapter region is can be proximal to the 3' end of the barcode region. As shown in FIG. 3B, the homopolymer region is positioned between the target region and the barcode region, with the barcode region proximal to the 3' end of the homopolymer region.

At step 304 of FIG. 3A and FIG. 3B, the sequence of the barcode region is determined using labeled nucleotides, for example using a flow sequencing method. In some embodiments, both labeled and unlabeled nucleotides are used. In some embodiments, the presence or absence of nucleotide incorporation during primer extension within the homopolymer region is not detected.

At step 306 of FIG. 3A and FIG. 3B, the primer is extended within the homopolymer region using labeled nucleotides complementary to the base present in the homopolymer region, thereby stalling primer extension within the homopolymer region. In some embodiments, both nucleotides include both labeled and unlabeled nucleotides. The proportion of labeled nucleotides to total nucleotides used to extend the primer is greater than the proportion used to extend the primer within the barcode region, thus stalling primer extension within the homopolymer region.

At step 308 of FIG. 3A and FIG. 3B, primer extension within the homopolymer region is continued using unlabeled nucleotides complementary to the base present in the homopolymer region after the primer extension stalled within the homopolymer region. Optionally, labeled nucleotides are also used to extend the primer within the homopolymer region, although the proportion of labeled nucleotides used to continue primer extension within the homopolymer region after stalling the primer extension should be lower than the proportion used when stalling the primer extension, and may further be lower than the proportion used when determining a sequence of a region (e.g., a barcode and/or target region).

Once the primer has been extended through the homopolymer region, the sequence of the target region is determined using nucleotides, as shown in step 310 in FIG. 3A and FIG. 3B, for example using a flow sequencing method. At least a portion of the nucleotides are labeled during sequencing. In some embodiments, the nucleotides comprise labeled nucleotides and unlabeled nucleotides. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Barcode Regions with Common Flow Length

The different barcode regions across the polynucleotides and the flow sequencing cycles used to sequence the different barcode regions can be configured s such that the primer is extended to the end of the barcode region across the plurality of polynucleotides before being extended into the homopolymer region. This does not require that the barcodes be of the same physical length (i.e., same number of bases), only that the flow length, as determined by the barcode sequences and the cycle order, of the different barcode regions be the same. The flow length of a region is the number of cycles needed to extend the primer from the start of the region to the end of the region. In this manner, the primer is extended to the start of a homopolymer region within the same flow cycle so that primer extension within the homopolymer region is initiated at the same time across the polynucleotides.

In some embodiments, the barcode region is proximal to the 3' end of the homopolymer region. In some embodiments, there are no intervening bases between the barcode region and the homopolymer region. The last base in the barcode regions is generally different from the base within the homopolymer region.

The cycles and the order of the cycles can be predetermined prior to the start of sequencing the barcode region. However, the cycles used during sequencing of the barcode region may be the same (i.e., symmetrical cycles) or different (i.e., asymmetrical cycles). Further, a given cycle need not include all four different bases (i.e., A, T, C, G), but may include two, three, or four different bases. That is, the cycles may be symmetrical cycles or asymmetrical cycles. However, as discussed above, no base is repeated within the same cycle.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, and wherein the target region is associated with a unique barcode region; (b) determining the sequence of the barcode region using labeled nucleotides in a plurality of predetermined cycles, wherein the predetermined cycles and the barcode regions of the polynucleotides are configured such that the primer is extended to the end of the barcode region across the plurality of polynucleotides before being extended into the homopolymer region; (c) extending the primer within the homopolymer region using unlabeled nucleotides; and (d) determining the sequence of the target region using labeled nucleotides.

In some embodiments, there is a method of determining a sequence of a region of interest from an mRNA molecule, comprising: (a) hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, and wherein the target region is associated with a unique barcode region; (b) determining the sequence of the barcode region using labeled non-terminating nucleotides in a plurality of predetermined cycles, wherein the predetermined cycles and the barcode regions of the polynucleotides are configured such that the primer is extended to the end of the barcode region across the plurality of polynucleotides before being extended into the homopolymer region; (c) extending the primer within the homopolymer region using unlabeled non-terminating nucleotides; and (d) determining the sequence of the target region using labeled non-terminating nucleotides.

Once the hybridized templates are formed, the primer can be extended through the barcode region, for example using a flow sequencing method. During sequencing of the barcode region, the primer is extended by contacting the hybridized templates with the nucleotides (comprising the labeled nucleotides and, in some embodiments, the unlabeled nucleotides). Different nucleotide types (e.g., A, C, G, or T) may be discretely contacted with the hybridized template within a given cycle, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. The barcode regions are sequenced using a plurality of predetermined cycles. The cycles used to sequence the barcode region may have the same (i.e., symmetrical) or different (i.e., asymmetrical) order of nucleotide types, which are optionally discretely used. This process is repeated for the predetermined cycles until the sequence of the barcode region is determined. The predetermined cycles and the sequence of the barcode regions are configured s such that the primer is extended to the end of the barcode region across the plurality of polynucleotides before being extended into the homopolymer region. This controls primer extension such that extension of the primer into the homopolymer region for any given polynucleotide does not occur without extension of the primer into the homopolymer region for all polynucleotides in the plurality.

Since extension of the primer is controlled at the end of the barcode region and before extending the primer into the homopolymer region, the proportion of labeled nucleotides used to extend the primer within the homopolymer region can be controlled. For example, primer extension within the homopolymer region can use a different proportion of labeled nucleotides than the proportion used to extend the primer within the barcode region and/or target region. In some embodiments, unlabeled nucleotides are used to extend the primer within the homopolymer region. In some embodiments, labeled nucleotides are used to extend the primer within the homopolymer region. In some embodiments, both labeled and unlabeled nucleotides are used to extend the primer within the homopolymer region. In some embodiments, labeled nucleotides are not used when extending the primer within the homopolymer region after stalling the primer within the homopolymer region. In some embodiments, less than about 5%, less than about 4%, less than about 3%, less than about 2%, less than about 1%, less than about 1%, less than about 0.5%, less than about 0.1%, less than about 0.05%, or less than about 0.01% of the total nucleotides used to extend within the homopolymer region.

Although the probability of primer extension stall is reduced by reducing or eliminating the proportion of labeled nucleotides, primer extension may still stall within the homopolymer region after reducing the proportion of labeled nucleotides relative to the proportion included when the primer extension was intentionally stalled. To re-start primer extension after stalling, unincorporated nucleotides and the polymerase can be removed (for example, by washing the hybridized templates), and then again contacting the hybridized templates with fresh, unlabeled nucleotides and polymerase. This process may be repeated 1, 2, 3, 4, or more times until the primer is extended through the homopolymer region.

The primer can be extended to the end of homopolymer region and to the start of the target region. As the target region includes the sequence associated with the mRNA region of interest, the sequence of the target region is determined, for example using a flow sequencing method. A polymerase can be used to incorporate labeled nucleotide onto the 3' end of the primer in a template-dependent manner, thereby extending the primer from the end of the homopolymer region and into the target region. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Figure 4A:
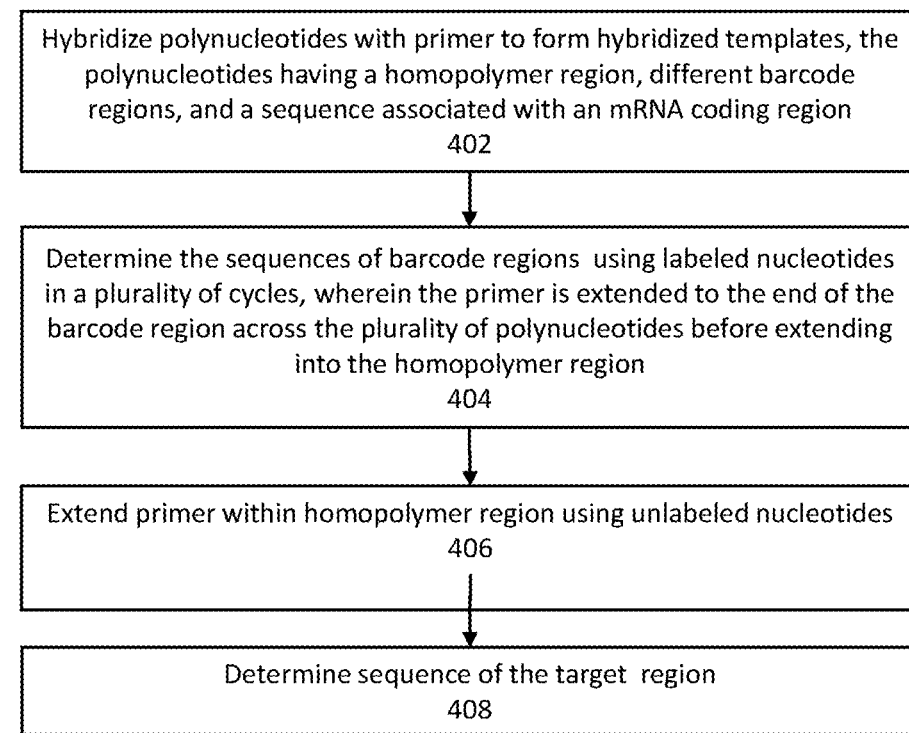
FIG. 4A shows an flow chart of an exemplary method for determining a sequence of a region of interest from an mRNA molecule, wherein flow cycles and the different barcode regions of the polynucleotides configured are such that the primer is extended to the end of the barcode region across the plurality of polynucleotides before being extended into the homopolymer region.
Figure 4B:
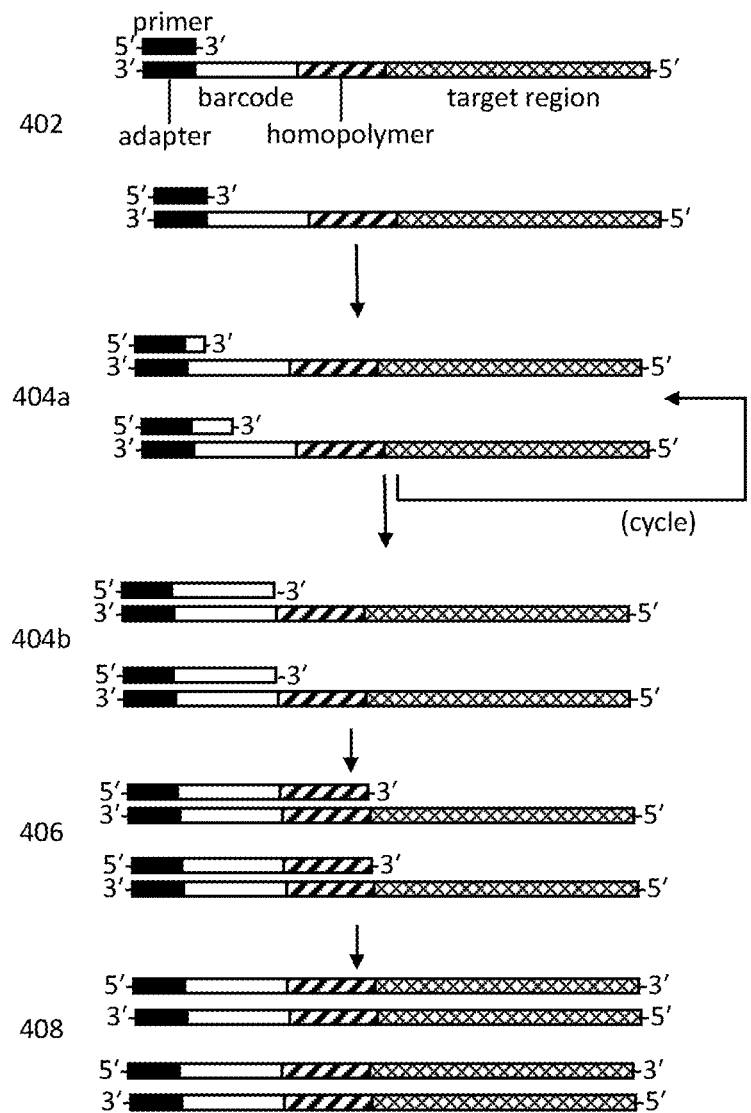
FIG. 4B shows an exemplary method for determining a sequence of a region of interest from an mRNA molecule, in graphical form, with multiple polynucleotides having different barcode region sequences but the same flow length.

FIG. 4A shows an flow chart of an exemplary method for determining a sequence of a region of interest from an mRNA molecule, wherein flow cycles and the different barcode regions of the polynucleotides configured are such that the primer is extended to the end of the barcode region across the plurality of polynucleotides before being extended into the homopolymer region. FIG. 4B shows an exemplary method in graphical form, with multiple polynucleotides having different barcode region sequences but the same flow length. At step 402, polynucleotides having a homopolymer region, a barcode region, and a target region comprising a sequence associated with (e.g., complementary to or identical to) an mRNA region of interest are hybridized to a primer to form hybridized templates. The different polynucleotides contain different barcode regions and different target regions such that the different target regions across the polynucleotides are associated with a unique molecular identifier. The 3' end of the polynucleotide can include an adapter region, and the primer can hybridize to the adapter region of the polynucleotide. The adapter region is proximal to the 3' end of the barcode region. As shown at 402 of FIG. 4B, the homopolymer region is positioned between the target region and the barcode region, with the barcode region proximal to the 3' end of the homopolymer region.

At step 404 of FIG. 4A, the sequences of the barcode regions are determined using labeled nucleotides, for example using a flow sequencing method. In some embodiments, both labeled and unlabeled nucleotides are used. The predetermined cycles and the different barcode regions of the polynucleotides are configured such that the primer is extended to the end of the barcode region across the plurality of polynucleotides before being extended into the homopolymer region Turning to FIG. 4B, at 404a, the primer hybridized to the polynucleotide is extended within the barcode region by contacting the hybridized template with different labeled nucleotide types, which are optionally discretely used. A polymerase extends the primer in a template-dependent manner, when a complement base is present in the template strand. Unincorporated nucleotides are removed, and the presence or absence of an incorporated nucleotide is detected to obtain sequencing information. This process is repeated using predetermined cycles to continue primer extension until the primer is extended to the start of the homopolymer region. As shown at 404b of FIG. 4B, the primer is extended through the barcode region across the plurality of polynucleotides before the primer is extended into the homopolymer region.

The primer is not extended within the homopolymer region across the polynucleotides until the primer has been extended through the different barcode regions. However, once the primer has been extended through the barcode regions, the primer can be extended within the homopolymer region using nucleotides, as shown in 406 of FIG. 4A and FIG. 4B. The nucleotides may be labeled, unlabeled, or a mixture of both labeled and unlabeled nucleotides. Because the sequence of the homopolymer region is generally uninteresting, the primer can be extended within the homopolymer region without detecting the presence or absence of nucleotide incorporation, for example by using unlabeled nucleotides or not detecting the label (e.g., fluoresce). Labeled nucleotides are generally more expensive and have an increased risk of the primer extension stalling, so the labeled nucleotides may be included as a smaller proportion of the total nucleotides (compared to the portion used to determine the sequence of the barcode region) or eliminated during the primer extension through the homopolymer region. In the event primer extension stalls within the homopolymer region, unincorporated nucleotides can be removed, for example by washing the hybridized templates, and fresh nucleotides complementary to the base present in the homopolymer region can be added.

Once the primer has been extended through the homopolymer region, the sequence of the target region is determined using nucleotides, as shown in step 410 in FIG. 4A and FIG. 4B, for example using a flow sequencing method. At least a portion of the nucleotides are labeled during sequencing. In some embodiments, the nucleotides comprise labeled nucleotides and unlabeled nucleotides. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Dual Primer Sequencing

In some embodiments, two primers are used to determine the sequence of a region of interest from an mRNA molecule, with a first primer being extended to sequence the barcode region and a second primer being extended to sequence the target region. The second primer hybridizes within the homopolymer region of the polynucleotide to avoid or limit primer extension within the homopolymer region. The order of primer hybridization and extension is reversible. That is, extension of the first primer to determine the sequence of the barcode region may occur before or after extension of the second primer to determine the sequence of the target region. Thus, the description of "first primer" and "second primer" provided below are provided only for clarity, and the sequence of the primers may be reversed.

The second primer comprises a homopolymer region comprising bases complementary to the bases in the homopolymer of the polynucleotide comprising the target region. For example, the second primer may comprise a poly-A region if the homopolymer region of the polynucleotide comprising the target region is a poly-T region, or the second primer may comprise a poly-T region if the homopolymer region of the polynucleotide comprising the target region is a poly-A region. This allows the second primer to efficiently hybridize to the homopolymer region of the polynucleotide. The homopolymer region of the primer may be longer, shorter, or approximately the same length as the homopolymer region of the polynucleotide.

In some embodiments, the 3' end of the second primer does not hybridize to the 5' end of the homopolymer region in the polynucleotide comprising the target region across the plurality of polynucleotides. The primer hybridized to the homopolymer region can therefore extended within the homopolymer region, thereby aligning the 3' end of the primer to the 5' end of the homopolymer region of the polynucleotide. The primer may be extended through the homopolymer region using labeled, unlabeled, or a mixture of labeled nucleotides. In the event primer extension stalls within the homopolymer region, unincorporated nucleotides can be removed, for example by washing the hybridized templates, and fresh nucleotides complementary to the base present in the homopolymer region can be added. Once the primer has extended through the homopolymer region of the polynucleotide, the target region of the polynucleotide can be sequenced by further extending the primer within the target region.

In some embodiments, the second primer comprises a homopolymer region comprising bases complementary to the bases in the homopolymer of the polynucleotide comprising the target region, and a 3' anchor. The 3' anchor increases the likelihood that the 3' end of the homopolymer region of the second primer hybridizes with the 5' end of the homopolymer region of the polynucleotide. The 3' anchor may include, for example, a base other than the base present in the homopolymer region of the second primer. The variable base can then hybridize to the first base after the 5' end of the homopolymer region of the polynucleotide (i.e., the first base of the target region). For example, if the homopolymer region of the polynucleotide is a poly-A sequence, the second primer may include a 5'-(poly-T)-V-3' sequence, wherein V is any base other than T (i.e., G, C, or A).

In some embodiments, the second primer comprises a homopolymer region comprising bases complementary to the bases in the homopolymer of the polynucleotide comprising the target region, and a 5' anchor. Optionally, the second primer may include both a 3' anchor and a 5' anchor. The 5' anchor can include, for example, a polynucleotide sequence complementary to an adapter sequence on the polynucleotide (which can be, for example, positioned proximal to the 3' end of the barcode region). With a 5' anchor, the homopolymer region of the second primer is more likely to hybridize closer to the 3' end of homopolymer region. The homopolymer region and the 5' anchor can be joined by a linker, for example a PEG phosphoramidite linker or an abasic deoxyribose or abasic ribose linker. The length of the linker may be, for example, approximately the same length as the barcode region, longer than the barcode region, or shorter than the barcode region.

The first primer can hybridize to the polynucleotide comprising the barcode region and the target region at a position proximal to the 3' end of the barcode region. For example, the polynucleotide can include a 3' adapter region, and the first primer can hybridize to the adapter region. The first primer is extended within the barcode region to determine the sequence of the barcode region.

In some embodiments, the first primer is removed from the hybridized template prior to hybridizing the second primer to the polynucleotide. The primer may be removed, for example, using a high pH solution, such as a sodium hydroxide solution. In some embodiments, the first primer is not removed from the hybridized template prior to hybridizing the second primer to the polynucleotide.

In some embodiments, a method of determining a sequence of a region of interest from an mRNA molecule, comprising: (a) hybridizing a plurality of polynucleotides derived from mRNA with a first primer to form a first plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled nucleotides; (c) hybridizing the plurality of polynucleotides with a second primer to form a second plurality of hybridized templates, wherein the second primer comprises a homopolymer region comprising a plurality of contiguous and identical bases complementary to the bases in the homopolymer region of the polynucleotides; and (d) determining the sequence of the target region using labeled nucleotides. In some embodiments, the second primer is extended within the homopolymer region using nucleotides (which may be labeled, unlabeled, or a mixture thereof). In some embodiments, the first primer is hybridized to the polynucleotide before the second primer is hybridized to the polynucleotide. In some embodiments, the second primer is hybridized to the polynucleotide before the first primer is hybridized to the polynucleotide.

In some embodiments, a method of determining a sequence of a region of interest from an mRNA molecule, comprising: (a) hybridizing a plurality of polynucleotides derived from mRNA with a first primer to form a first plurality of hybridized templates, the polynucleotides comprising a barcode region, a homopolymer region comprising a plurality of contiguous and identical bases, and a target region comprising a sequence associated with a region of interest from an mRNA molecule; (b) determining the sequence of the barcode region using labeled non-terminating nucleotides; (c) hybridizing the plurality of polynucleotides with a second primer to form a second plurality of hybridized templates, wherein the second primer comprises a homopolymer region comprising a plurality of contiguous and identical bases complementary to the bases in the homopolymer region of the polynucleotides; and (d) determining the sequence of the target region using labeled non-terminating nucleotides. In some embodiments, the second primer is extended within the homopolymer region using non-terminating nucleotides (which may be labeled, unlabeled, or a mixture thereof). In some embodiments, the first primer is hybridized to the polynucleotide before the second primer is hybridized to the polynucleotide. In some embodiments, the second primer is hybridized to the polynucleotide before the first primer is hybridized to the polynucleotide.

Figure 5A:
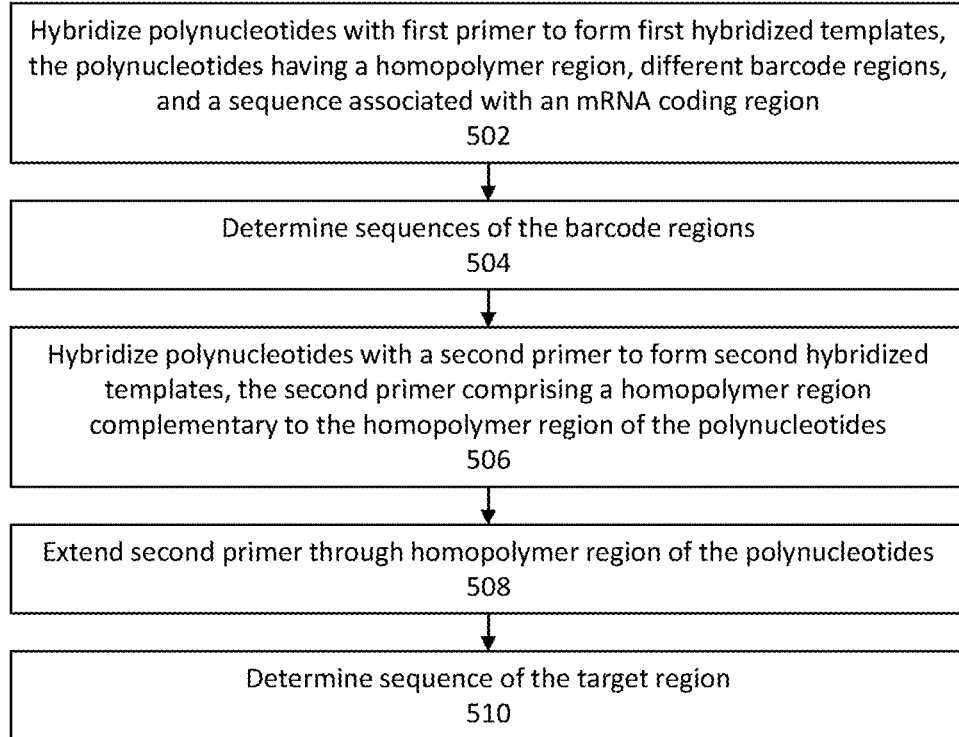
FIG. 5A shows an flow chart of an exemplary method for determining a sequence of a region of interest from an mRNA molecule using two primers.
Figure 5B:
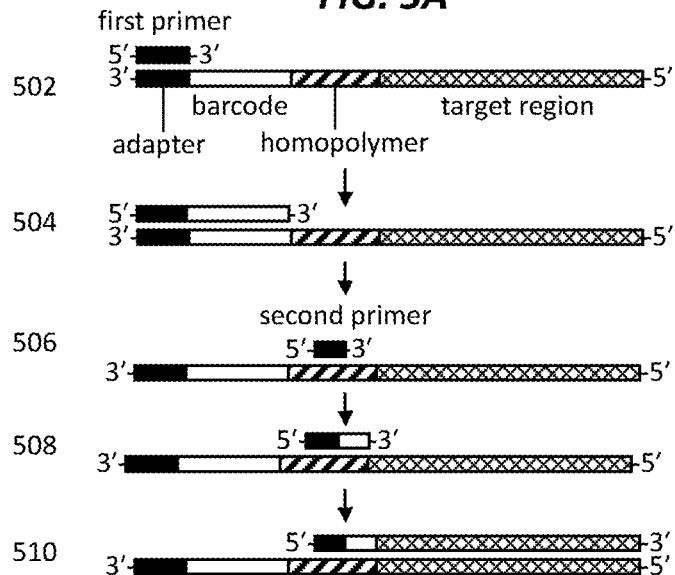
FIG. 5B shows an exemplary method for determining a sequence of a region of interest from an mRNA molecule using two primers, in graphical form.

FIG. 5A shows an flow chart of an exemplary method for determining a sequence of a region of interest from an mRNA molecule using two primers. FIG. 5B shows an exemplary method in graphical form. At step 502, polynucleotides having a homopolymer region, a barcode region, and a target region comprising a sequence associated with (e.g., complementary to or identical to) an mRNA region of interest are hybridized to a first primer to form first hybridized templates. The different polynucleotides contain different barcode regions and different target regions such that the different target regions across the polynucleotides are associated with a unique molecular identifier. The 3' end of the polynucleotide can include an adapter region, and the primer can hybridize to the adapter region of the polynucleotide. The adapter region is can be proximal to the 3' end of the barcode region. As shown in FIG. 5B, the homopolymer region is positioned between the target region and the barcode region, with the barcode region proximal to the 3' end of the homopolymer region.

At step 504 of FIG. 5A and FIG. 5B, the sequence of the barcode region is determined by extending the first primer using labeled nucleotides, for example using a flow sequencing method. The labeled nucleotides are optionally combined with unlabeled nucleotides. During sequencing of the barcode region, the primer is extended by contacting the hybridized templates with the nucleotides (comprising the labeled nucleotides and, optionally, the unlabeled nucleotides) in a defined order. Nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined.

At step 506 of FIG. 5A and FIG. 5B, the polynucleotide is hybridized to a second primer comprising a homopolymer region with bases complementary to the bases present in the homopolymer region of the polynucleotides, thereby forming second hybridized templates. Optionally, the first primer is removed prior to hybridizing the second primer to the polynucleotides. In some embodiments, the second primer is extended within the homopolymer region so that the 3' end of the primer is positioned at the 5' end of the homopolymer region of the polynucleotide, as shown in step 508. This can be done, for example, by template-dependent extension of the primer. Unlabeled and/or labeled nucleotides complementary to the base present in the homopolymer region can be contacted with the second hybridized templates and incorporated onto the end of the second primer, for example using a polymerase, thereby extending the second primer. Step 508 is not always needed, as the second primer may be configured such that the 3' end of the primer is positioned at the 5' end of the homopolymer region of the polynucleotide upon hybridization, for example through the use of a 3' anchor.

The second primer is extended into the target region using labeled (and, optionally, unlabeled) nucleotides, for example using the flow sequencing methods described herein, thereby determining the sequence of the target region, as shown at step 510 of FIG. 5A and FIG. 5B. During sequencing of the barcode region, the primer is extended by contacting the hybridized templates with the nucleotides (comprising the labeled nucleotides and, optionally, the unlabeled nucleotides) in a defined order. Nucleotide types (e.g., A, C, G, or T) are optionally discretely contacted with the second hybridized templates, or two or three different nucleotide types may be simultaneously used. A polymerase can be used to incorporate the nucleotide onto the 3' end of the second primer in a template-dependent manner, thereby extending the second primer. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Figure 5C:
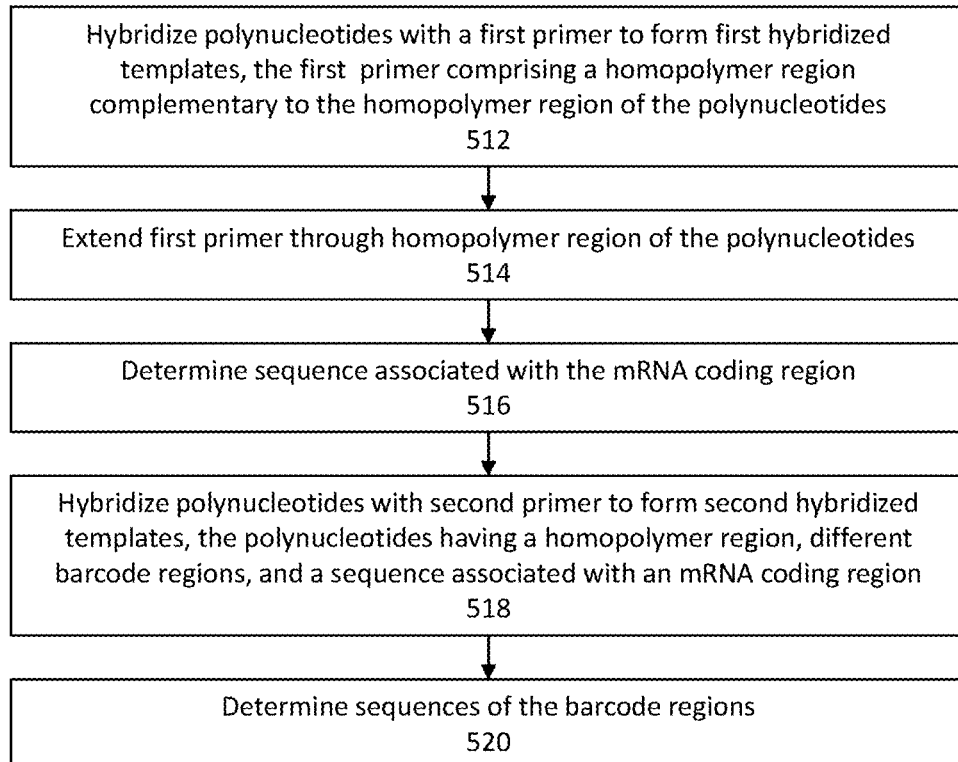
FIG. 5C shows an flow chart of another exemplary method for determining a sequence of a region of interest from an mRNA molecule using two primers, wherein the sequence of the two primers hybridized to the polynucleotides is reversed compared to the exemplary method shown in FIG. 5A.
Figure 5D:
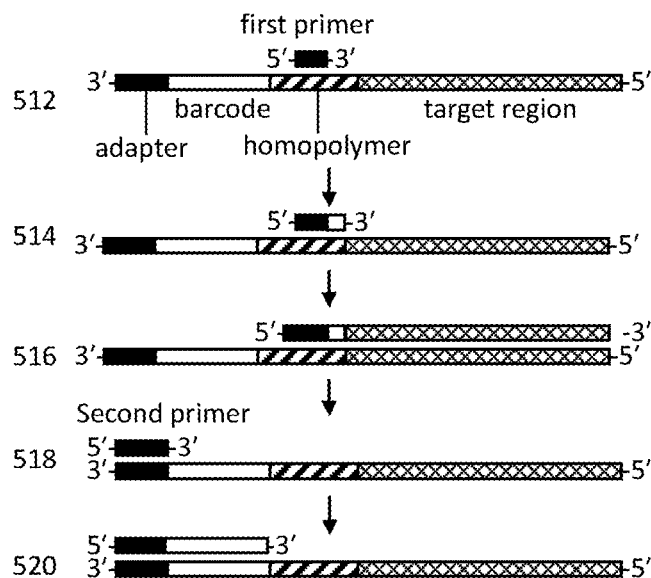
FIG. 5D shows an exemplary method for determining a sequence of a region of interest from an mRNA molecule using two primers, wherein the sequence of the two primers hybridized to the polynucleotides is reversed compared to the exemplary method shown in FIG. 5A, in graphical form.

FIG. 5C shows an flow chart of another exemplary method for determining a sequence of a region of interest from an mRNA molecule using two primers, wherein the sequence of the two primers hybridized to the polynucleotides is reversed compared to the exemplary method shown in FIG. 5A. FIG. 5D shows an exemplary method in graphical form. At step 512 of FIG. 5C and FIG. 5D, having a homopolymer region, a barcode region, and a target region comprising a sequence associated with (e.g., complementary to or identical to) an mRNA region of interest are hybridized to a first primer to form hybridized templates. The first primer comprises a homopolymer region with bases complementary to the bases present in the homopolymer region of the polynucleotides. In some embodiments, the second primer is extended within the homopolymer region so that the 3' end of the primer is positioned at the 5' end of the homopolymer region of the polynucleotide, as shown in step 514. This can be done, for example, by template-dependent extension of the primer. Unlabeled and/or labeled nucleotides complementary to the base present in the homopolymer region can be contacted with the second hybridized templates and incorporated onto the end of the second primer, for example using a polymerase, thereby extending the first primer.

The first primer is extended into the target region using labeled (and, optionally, unlabeled) nucleotides, for example using a flow sequencing method, thereby determining the sequence of the target region, as shown at step 516 of FIG. 5C and FIG. 5D. During sequencing of the target region, the first primer is extended by contacting the first hybridized templates with the nucleotides (comprising the labeled nucleotides and, optionally, the unlabeled nucleotides) in a defined order. Nucleotide types (e.g., A, C, G, or T) may be discretely contacted with the first hybridized templates, or two or more different nucleotide types may be simultaneously used. A polymerase can be used to incorporate the nucleotide onto the 3' end of the first primer in a template-dependent manner, thereby extending the first primer. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

At step 518 of FIG. 5C and FIG. 5D, the polynucleotides are hybridized to a second primer to form second hybridized templates. Optionally, the extended first primer is removed before the second primer is hybridized to the polynucleotides. The different polynucleotides contain different barcode regions and different target regions such that the different target regions across the polynucleotides are associated with a unique molecular identifier. The 3' end of the polynucleotide can include an adapter region, and the primer can hybridize to the adapter region of the polynucleotide. The adapter region is can be proximal to the 3' end of the barcode region. As shown in FIG. 5D, the homopolymer region is positioned between the target region and the barcode region, with the barcode region proximal to the 3' end of the homopolymer region.

At step 520 of FIG. 5C and FIG. 5D, the sequence of the barcode region is determined by extending the second primer using labeled nucleotides, for example using a flow sequencing method. The labeled nucleotides are optionally combined with unlabeled nucleotides. During sequencing of the barcode region, the second primer is extended by contacting the second hybridized templates with the nucleotides (comprising the labeled nucleotides and, optionally, the unlabeled nucleotides) in a defined order. Nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined.

Primer with a Cleavable Linker

In some embodiments, primer with a cleavable linker is used to determine the sequence of a region of interest from an mRNA molecule. The primer includes a first primer segment, a second primer segment comprising a homopolymer region comprising a plurality of bases complementary to the bases in the homopolymer region of the polynucleotides, and a cleavable linker between the first primer segment and the second primer segment. The first primer segment is proximal to the 3' end of the primer, and the second primer segment is proximal to the 5' end of the primer.

The second primer segment can be extended to sequence the target region of the polynucleotide, for example using a flow sequencing method. As further discussed herein, in some embodiments, the second primer segment is extended to the end of the homopolymer region of the polynucleotide prior to extending the primer into the target region and determining the sequence of the primer region. The cleavable linker can then be cleaved, and the first segment of the primer can be extended to sequence the barcode region of the polynucleotide, for example using a flow sequencing method.

The second primer segment comprises a homopolymer region comprises bases complementary to the bases in the homopolymer of the polynucleotide comprising the target region. For example, the second primer may comprise a poly-A region if the homopolymer region of the polynucleotide comprising the target region is a poly-T region, or the second primer may comprise a poly-T region if the homopolymer region of the polynucleotide comprising the target region is a poly-A region. This allows the second primer to efficiently hybridize to the homopolymer region of the polynucleotide. The homopolymer region of the primer may be longer, shorter, or approximately the same length as the homopolymer region of the polynucleotide.

In some embodiments, the 3' end of the second primer segment does not hybridize to the 5' end of the homopolymer region in the polynucleotide comprising the target region across the plurality of polynucleotides. The second primer segment can be extended within the homopolymer region, thereby aligning the 3' end of the primer to the 5' end of the homopolymer region of the polynucleotide. The second primer segment may be extended through the homopolymer region using labeled, unlabeled, or a mixture of labeled nucleotides. In the event primer extension stalls within the homopolymer region, unincorporated nucleotides can be removed, for example by washing the hybridized templates, and fresh nucleotides complementary to the base present in the homopolymer region can be added. Once the second primer segment has been extended through the homopolymer region of the polynucleotide, the target region of the polynucleotide can be sequenced by further extending the primer within the target region.

In some embodiments, the second primer segment comprises a homopolymer region comprising bases complementary to the bases in the homopolymer of the polynucleotide comprising the target region, and a 3' anchor. The 3' anchor increases the likelihood that the 3' end of the homopolymer region of the second primer segment hybridizes with the 5' end of the homopolymer region of the polynucleotide. The 3' anchor may include, for example, a base other than the base present in the homopolymer region of the second primer segment. The variable base can then hybridize to the first base after the 5' end of the homopolymer region of the polynucleotide (i.e., the first base of the target region). For example, if the homopolymer region of the polynucleotide is a poly-A sequence, the second primer may include a 5'-(poly-T)-V-3' sequence, wherein V is any base other than T (i.e., G, C, or A).

The cleavable linker may be any suitable linker that covalently links the first primer segment and the second primer segment for which cleavage can be controlled. In some embodiments, the cleavable linker includes a polynucleotide sequence comprising a uracil (U) base. The uracil base can be controllably cleaved using a uracil-specific cleaving enzyme (e.g., the uracil-specific excision reagent (USER®) enzyme, available from New England BioLabs). Since the uracil base is unique to RNA, there is no risk of cleaving DNA polynucleotides or primers.

The first primer segment is configured to hybridize to a sequence (e.g., an adapter sequence) proximal to the 5' end of the barcode region. Once the primer has been cleaved, the 3' end of the first primer segment can be extended to determine the sequence of the barcode region, for example by using a flow sequencing method.

In some embodiments, a method of determining a sequence of a region of interest from an mRNA molecule, comprising: (a) hybridizing a plurality of polynucleotides derived from mRNA with a primer to form a plurality of hybridized templates; polynucleotides comprising a barcode region, a homopolymer region comprising a plurality of contiguous and identical bases, and a target region comprising a sequence associated with a region of interest from an mRNA molecule; wherein the primer comprises a first primer segment, a second primer segment comprising a homopolymer region comprising a plurality of bases complementary to the bases in the homopolymer region of the polynucleotides, and a cleavable linker between the first primer segment and the second primer segment; (b) determining the sequence of the target region using labeled nucleotides; (c) cleaving the primer at the cleavable linker; and (d) determining the sequence of the barcode region using labeled nucleotides.

In some embodiments, a method of determining a sequence of a region of interest from an mRNA molecule, comprising: (a) hybridizing a plurality of polynucleotides derived from mRNA with a primer to form a plurality of hybridized templates; polynucleotides comprising a barcode region, a homopolymer region comprising a plurality of contiguous and identical bases, and a target region comprising a sequence associated with a region of interest from an mRNA molecule; wherein the primer comprises a first primer segment, a second primer segment comprising a homopolymer region comprising a plurality of bases complementary to the bases in the homopolymer region of the polynucleotides, and a cleavable linker between the first primer segment and the second primer segment; (b) determining the sequence of the target region using labeled non-terminating nucleotides; (c) cleaving the primer at the cleavable linker; and (d) determining the sequence of the barcode region using labeled non-terminating nucleotides.

Figure 6A:
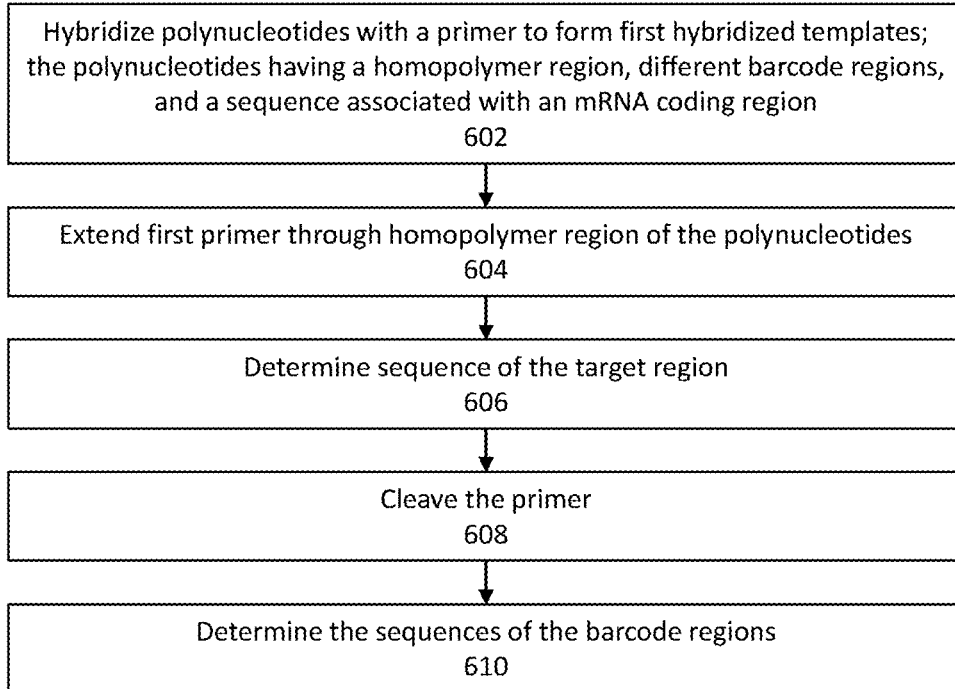
FIG. 6A shows an flow chart of an exemplary method for determining a sequence of a region of interest from an mRNA molecule using a cleavable primer.
Figure 6B:
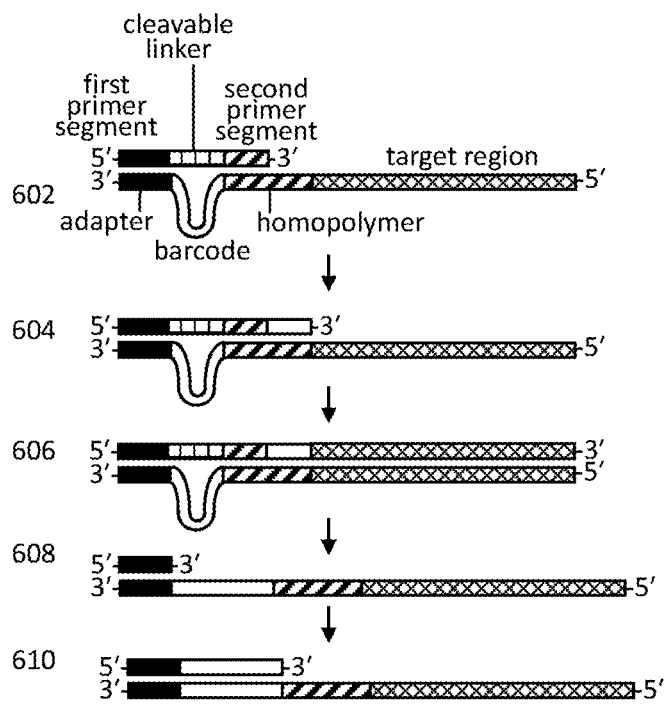
FIG. 6B shows an exemplary method for determining a sequence of a region of interest from an mRNA molecule using a cleavable primer, in graphical form.

FIG. 6A shows an flow chart of an exemplary method for determining a sequence of a region of interest from an mRNA molecule using a cleavable primer. FIG. 6B shows an exemplary method in graphical form. At step 602, polynucleotides having a homopolymer region, a barcode region, and a target region comprising a sequence associated with (e.g., complementary to or identical to) an mRNA region of interest are hybridized to a primer to form hybridized templates. The primer includes a first primer segment, a second primer segment comprising a homopolymer region comprising a plurality of bases complementary to the bases in the homopolymer region of the polynucleotides, and a cleavable linker between the first primer segment and the second primer segment. The different polynucleotides contain different barcode regions and different target regions such that the different target regions across the polynucleotides are associated with a unique molecular identifier. The 3' end of the polynucleotide can include an adapter region, and the first primer segment can hybridize to the adapter region of the polynucleotide. The adapter region is proximal to the 3' end of the barcode region. As shown in FIG. 6B, the homopolymer region is positioned between the target region and the barcode region, with the barcode region proximal to the 3' end of the homopolymer region.

In some embodiments, the second primer segment is extended within the homopolymer region so that the 3' end of the primer is positioned at the 5' end of the homopolymer region of the polynucleotide, as shown in step 604. This can be done, for example, by template-dependent extension of the primer. Unlabeled and/or labeled nucleotides complementary to the base present in the homopolymer region can be contacted with the second hybridized templates and incorporated onto the end of the second primer, for example using a polymerase, thereby extending the second primer. Step 504 is not always needed, as the second primer may be configured such that the 3' end of the primer is positioned at the 5' end of the homopolymer region of the polynucleotide upon hybridization, for example through the use of a 3' anchor.

The primer is extended into the target region using labeled (and, optionally, unlabeled) nucleotides, for example using a flow sequencing method, thereby determining the sequence of the target region, as shown at step 606 of FIG. 6A and FIG. 6B. During sequencing of the target region, the first primer is extended by contacting the hybridized templates with the nucleotides (comprising the labeled nucleotides and, optionally, the unlabeled nucleotides) in a defined order. Nucleotide types (e.g., A, C, G, or T) may be discretely contacted with the first hybridized templates, or two or three different nucleotide types may be simultaneously used. A polymerase can be used to incorporate the nucleotide onto the 3' end of the first primer in a template-dependent manner, thereby extending the first primer. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

At step 608 of FIG. 6A and FIG. SB, the primer is cleaved at the cleavable linker. The cleavable linker can be contacted with a suitable cleavage reagent, which frees the 3' end of the first primer segment. Optionally, the second primer segment is removed, for example using a high pH solution (e.g., a solution containing sodium hydroxide).

At step 610 of FIG. 6A and FIG. 6B, the sequence of the barcode region is determined by extending the first primer segment using labeled nucleotides, for example using a flow sequencing method. The labeled nucleotides are optionally combined with unlabeled nucleotides. During sequencing of the barcode region, the second primer is extended by contacting the second hybridized templates with the nucleotides (comprising the labeled nucleotides and, optionally, the unlabeled nucleotides) in a defined order. Nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined.

Restarting Stalled Primer Extension

Primer extension within a long homopolymer region can result in stalling of the primer extension. The likelihood of primer extension stall is greater as the proportion of labeled nucleotides to total nucleotides increases, as the polymerase is generally better adapted for incorporating native or near-native nucleotides. Nevertheless, primer extension is prone to stall even when native nucleotides are used for primer extension given a sufficiently long enough homopolymer region, such the poly-A region of some mRNA molecules.

Removing unincorporated nucleotides and contacting the hybridized templates with fresh nucleotides can restart primer extension. In some cases, the hybridized templates are contacted with fresh nucleotides. This process may be repeated 1, 2, 3, 4, 5, or more times to ensure the primer is fully extended through the homopolymer region. This strategy may be employed in combination with the other strategies described herein, wherein extension of the primer may stall during extension of the primer within the homopolymer region. For example, the primer extension may stall and be restarted within the homopolymer region when the polynucleotide has a barcode region (such as a barcode region omitting a base present in the homopolymer region, a barcode region that has a common flow length with other barcode regions in a plurality of polynucleotides), when the primer extension is intentionally stalled within the homopolymer region (for example, by increasing the proportion of labeled nucleotides used to extend the primer), or when using a dual primer or cleavable primer system.

In some embodiments, a method of determining a sequence of a region of interest from an mRNA molecule includes: (a) hybridizing a plurality of polynucleotide derived from mRNA with a primer to form a plurality of hybridized templates, wherein the polynucleotides comprise a homopolymer region comprising a plurality of contiguous and identical bases and a target region comprising a sequence associated with a region of interest from an mRNA molecule; (b) extending the primer into the homopolymer region using nucleotides of the same base, wherein the primer stalls within the homopolymer region, and removing unincorporated nucleotides; (c) repeating step (b) one or more times to extend the primer through the homopolymer region; and (d) determining the sequence of the target region using labeled nucleotides.

In some embodiments, a method of determining a sequence of a region of interest from an mRNA molecule includes: (a) hybridizing a plurality of polynucleotide derived from mRNA with a primer to form a plurality of hybridized templates, wherein the polynucleotides comprise a homopolymer region comprising a plurality of contiguous and identical bases and a target region comprising a sequence associated with a region of interest from an mRNA molecule; (b) extending the primer into the homopolymer region using non-terminating nucleotides of the same base, wherein the primer stalls within the homopolymer region, and removing unincorporated non-terminating nucleotides; (c) repeating step (b) one or more times to extend the primer through the homopolymer region; and (d) determining the sequence of the target region using labeled non-terminating nucleotides.

Figure 7A:
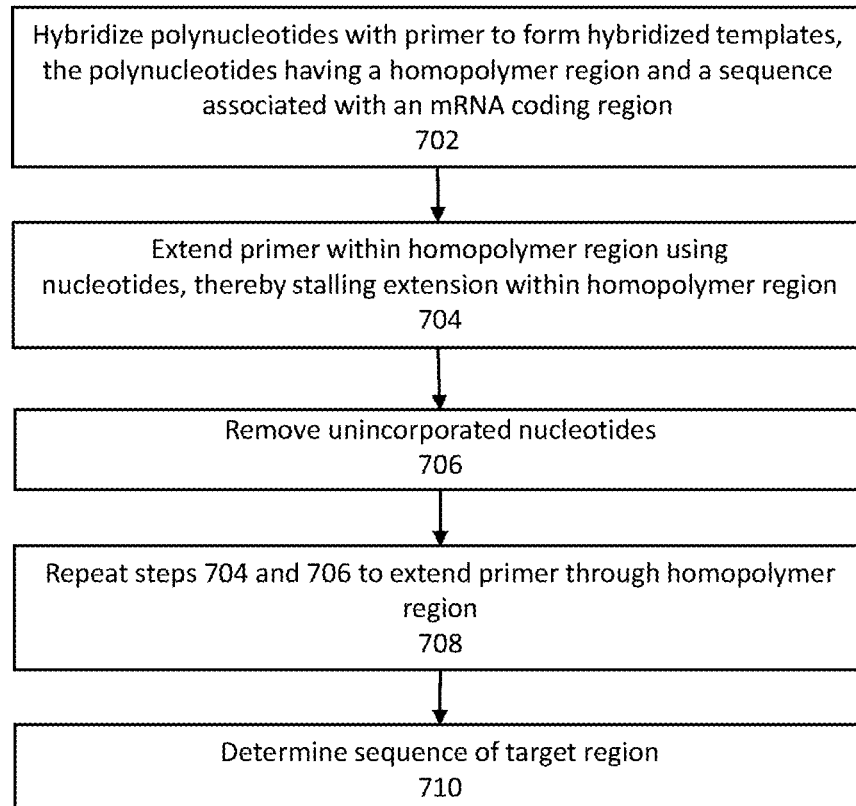
FIG. 7A shows an flow chart of an exemplary method for determining a sequence of a region of interest from an mRNA molecule, wherein primer extension is stalled and restarted within the homopolymer region of the polynucleotide.
Figure 7B:
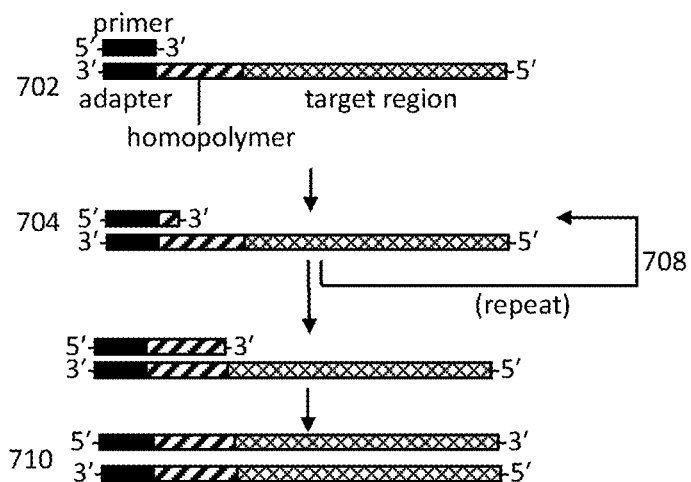
FIG. 7B shows an exemplary method for determining a sequence of a region of interest from an mRNA molecule, wherein primer extension is stalled and restarted within the homopolymer region of the polynucleotide, in graphical form.

FIG. 7A shows an flow chart of an exemplary method for determining a sequence of a region of interest from an mRNA molecule, wherein primer extension is stalled and restarted within the homopolymer region of the polynucleotide. FIG. 7B shows an exemplary method in graphical form. Although the exemplary method described below references a polynucleotide having a homopolymer region and a target region, the polynucleotide may further include additional regions, for example a barcode region proximal to the 3' end of the homopolymer region.

At step 702, polynucleotides having a homopolymer region and a target region comprising a sequence associated with (e.g., complementary to or identical to) an mRNA region of interest (and optionally, a barcode region, which is not shown in FIG. 7B) are hybridized to a primer to form hybridized templates. The 3' end of the polynucleotide can include an adapter region, and the primer can hybridize to the adapter region of the polynucleotide. The adapter region may be proximal to the 3' end of the barcode region, if present, or the 3' end of the homopolymer region.

If the barcode region is present, the sequence of the barcode region can be determined using nucleotides, for example using a flow sequencing method. During sequencing of the barcode region, the primer is extended by contacting the hybridized templates with the nucleotides (comprising labeled nucleotides and, optionally, unlabeled nucleotides) in a defined order. Nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the barcode region is determined.

At step 704 of FIG. 7A and FIG. 7B, the primer is extended within the homopolymer region using nucleotides complementary to the base present in the homopolymer region. In some embodiments, the nucleotides comprise labeled nucleotides, unlabeled nucleotides, or both labeled and unlabeled nucleotides. As discussed above, as the proportion of labeled nucleotides increases, the likelihood of primer extension stall increases. However, even when the nucleotides are entirely unlabeled, primer extension may stall when extended within longer homopolymer regions.

At step 706 of FIG. 7A, unincorporated nucleotides are removed. For example, the hybridized templates may be washed using a wash buffer. This step effectively "resets" the hybridized template such that primer extension can be restarted after stalling.

At step 708 of FIG. 7A and FIG. 7B, primer extension within the homopolymer region is restarted by repeating steps 704 and 706. Nucleotides complementary to the base present in the homopolymer region are used to further extend the primer within the homopolymer region. The nucleotides may be unlabeled, labeled or a mixture of labeled and unlabeled nucleotides. In some embodiments, labeled nucleotides are not used when extending the primer within the homopolymer region after stalling the primer within the homopolymer region. In some embodiments, less than about 5%, less than about 4%, less than about 3%, less than about 2%, less than about 1%, less than about 1%, less than about 0.5%, less than about 0.1%, less than about 0.05%, or less than about 0.01% of the total nucleotides used to continue extension of the primer within the homopolymer region after the primer extension has stalled are labeled nucleotides.

Steps 704 and 706 can be repeated 1, 2, 3, 4, 5 or more times to extend the primer through the homopolymer region. Primer extension need not have actually stalled or stalled on all polynucleotides in a plurality of polynucleotides for this method to be effective. Unincorporated nucleotides may be removed and fresh, nucleotides may be used to restart a polymerase after a stall or to pre-empt a stall. For example, the removal of unincorporated nucleotides and further primer extension using fresh nucleotides may be repeated periodically at regular or irregular intervals without regards the number of actual stalls, for example every 15 seconds, every 30 seconds, every 60 seconds, every 2 minutes, every 5 minutes, etc.

Once the primer has been extended through the homopolymer region, the sequence of the target region is determined using nucleotides, as shown in step 710 in FIG. 7A and FIG. 7B, for example using a flow sequencing method. At least a portion of the nucleotides are labeled during sequencing. In some embodiments, the nucleotides comprise labeled nucleotides and unlabeled nucleotides. During sequencing of the barcode region, the primer is extended by contacting the hybridized templates with the nucleotides (comprising labeled nucleotides and, optionally, unlabeled nucleotides) in a defined order. Different nucleotide types (e.g., A, C, G, or T) may be discretely contacted with the hybridized template, or two or three different nucleotide types may be simultaneously used. A polymerase can be used to incorporate the nucleotide onto the 3' end of the primer in a template-dependent manner, thereby extending the primer. Unincorporated nucleotides can be removed, for example by washing the hybridized templates. The presence or absence of an incorporated labeled nucleotide is then detected to determine the sequence at that position. This process is repeated using an order of nucleotides until the sequence of the target region is determined, thereby allowing the sequence of the region of interest from the mRNA molecule to be inferred.

Additional methods for recovering stalled sequencing primer extensions, including within homopolymer regions and non-homopolymer regions, are described in International PCT Application No. PCT/US2020/031196, the contents of which are incorporated herein by reference for all purposes.

EXAMPLES

The application may be better understood by reference to the following non-limiting examples, which is provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Sample cells are lysed using a lysis buffer, and liquid lysate separated using centrifugation. The separated liquid lysate is incubated with capture beads, each capture bead containing DNA oligomer containing a barcode region (containing a common sample barcode and a UMI) fused to the 5' of a poly-T region containing 10-30 consecutive thymine bases. mRNA molecules in the liquid lysate are isolated using the capture beads by separating and washing the capture beads. The mRNA molecules are reverse transcribed using the capture probe DNA oligomer and a reverse transcriptase, yielding a cDNA library. Each cDNA molecule in the cDNA library includes the barcode region with a sample barcode and a UMI, a homopolymer poly-T region, and a target region complementary to the mRNA region of interest (which includes at least a portion of a coding region). The barcode regions are specifically designed to omit adenine bases.

The cDNA library is prepared for sequencing by attaching adapter sequences to the 5' and 3' ends of the cDNA polynucleotides to generate a sequencing library. The sequencing library is applied to a sequencing array surface containing DNA oligonucleotides attached to the surface. The DNA oligonucleotides include sequences that hybridize to the adapter regions of the cDNA molecules. Sequencing colonies are formed by bridge amplification, which generates copies of the cDNA molecules and complements of the cDNA molecules.

A sequencing primer is applied to the sequencing surface, which hybridizes to adapter regions at the 3' end of the cDNA molecule complements. A DNA polymerase is also applied to the sequencing surface, and the DNA polymerase binds to the hybridized templates. A first solution containing a first nucleotides (e.g., deoxy-A, deoxy-G, or deoxy-C), such as non-terminating nucleotides, and the sequencing surface is washed to remove unincorporated nucleotides using a wash buffer. The nucleotides contain about 2.5% fluorescently labeled and about 97.5% unlabeled nucleotides. The presence or absence of base incorporation across the colonies is detected using a fluorescence detector. This process is repeated using a second solution and a third solution, each containing a different (i.e., second and third) nucleotides to complete a flow cycle, and the flow cycles are repeated to sequence the barcode region. The nucleotides in the second and third solutions contain about 2.5% fluorescently labeled and about 97.5% unlabeled nucleotides. During this process, no thymine bases are included in the cycle. The fluorescent label is cleaved from the growing polynucleotide after each imaging step.

Once the sequencing primer is extended through the barcode region, a fourth solution containing 100% unlabeled thymidine triphosphate is applied to the sequencing surface, which initiates extension of the primer through the homopolymer region. The surfaces is allowed to react for a period of time before the surface is washed with a wash buffer and the process repeated to eliminate stalled primer extension. This allows the primer to be extended through the poly-A homopolymer region and to the start of the target region of the cDNA molecule complements.

The first, second, and third solutions, in addition to a fifth solution containing thymine nucleotides (about 2.5% fluorescently labeled and about 97.5% unlabeled) are used to sequence the target region of the target region. The solutions are separately applied to the sequencing surface, the surface washed, and presence or absence of base incorporation detected before applying the next solution in a cycle, for a series of cycles. The fluorescent label is cleaved from the growing polynucleotide after each imaging step.

Example 2

Sample cells are lysed using a lysis buffer, and liquid lysate separated using centrifugation. The separated liquid lysate is incubated with capture beads, each capture bead containing DNA oligomer containing a barcode region (containing a common sample barcode and a UMI) fused to the 5' of a poly-T region containing 10-30 consecutive thymine bases. mRNA molecules in the liquid lysate are isolated using the capture beads by separating and washing the capture beads. The mRNA molecules are reverse transcribed using the capture probe DNA oligomer and a reverse transcriptase, yielding a cDNA library. Each cDNA molecule in the cDNA library includes the barcode region with a sample barcode and a UMI, a homopolymer poly-T region, and a target region complementary to the mRNA region of interest (which includes at least a portion of a coding region).

The cDNA library is prepared for sequencing by attaching adapter sequences to the 5' and 3' ends of the cDNA polynucleotides to generate a sequencing library. The sequencing library is applied to a sequencing array surface containing DNA oligonucleotides attached to the surface. The DNA oligonucleotides include sequences that hybridize to the adapter regions of the cDNA molecules. Sequencing colonies are formed by bridge amplification, which generates copies of the cDNA molecules and complements of the cDNA molecules.

A sequencing primer is applied to the sequencing surface, which hybridizes to adapter regions at the 3' end of the cDNA molecule complements. A DNA polymerase is also applied to the sequencing surface. A first solution containing a first nucleotides (e.g., deoxy-A, deoxy-G, deoxy-C, or deoxy-T), such as non-terminating nucleotides, and the sequencing surface is washed to remove unincorporated nucleotides using a wash buffer. The nucleotides contain about 2.5% fluorescently labeled and about 97.5% unlabeled nucleotides. The presence or absence of base incorporation across the colonies is detected using a fluorescence detector. This process is repeated using a second, third, and fourth solutions, each containing different (i.e., second, third, and fourth) nucleotides to complete a flow cycle, and the flow cycles are repeated to sequence the barcode region. The nucleotides in the second and third solutions contain about 2.5% fluorescently labeled and about 97.5% unlabeled nucleotides. The fluorescent label is cleaved from the growing polynucleotide after each imaging step.

Once the sequencing primer is extended through the barcode region, a fifth solution containing 80% labeled thymidine triphosphate is applied to the sequencing surface, which initiates extension of the primer within the homopolymer region before it quickly stalls. The sequencing surface is then washed to remove unincorporated nucleotides.

After primer extension stalls, a sixth solution containing 100% unlabeled thymidine triphosphate is applied to the sequencing surface, which initiates extension of the primer through the homopolymer region. The surfaces is allowed to react for a period of time before the surface is washed with a wash buffer and the process repeated to eliminate stalled primer extension. This allows the primer to be extended through the poly-A homopolymer region and to the start of the target region of the cDNA molecule complements.

The first, second, third and fourth solutions are used to sequence the target region of the target region. The solutions are separately applied to the sequencing surface, the surface washed, and presence or absence of base incorporation detected before applying the next solution in a cycle, for a series of cycles. The fluorescent label is cleaved from the growing polynucleotide after each imaging step.

Example 3

Sample cells are lysed using a lysis buffer, and liquid lysate separated using centrifugation. The separated liquid lysate is incubated with capture beads, each capture bead containing DNA oligomer containing a barcode region (containing a common sample barcode and a UMI) fused to the 5' of a poly-T region containing 10-30 consecutive thymine bases. mRNA molecules in the liquid lysate are isolated using the capture beads by separating and washing the capture beads. The mRNA molecules are reverse transcribed using the capture probe DNA oligomer and a reverse transcriptase, yielding a cDNA library. Each cDNA molecule in the cDNA library includes the barcode region with a sample barcode and a UMI, a homopolymer poly-T region, and a target region complementary to the mRNA region of interest (which includes at least a portion of a coding region).

The barcode regions are specifically designed in combination with a flow cycle design so that the barcode regions have the same flow length. Exemplary barcodes with a corresponding flowgram is shown in Table 2. The sequencing primer for each of the four barcodes is reaches the end of the barcode within of the fourth cycle.

TABLE 2

| Barcode | Cycle 1 | | | | Cycle 2 | | | |
|---|---|---|---|---|---|---|---|---|
| | A | C | T | G | A | C | T | G |
| TTTT | 1 | 0 | 0 | 0 | 1 | 0 | 0 | 0 |
| GGGG | 0 | 1 | 0 | 0 | 0 | 1 | 0 | 0 |
| AAAA | 0 | 0 | 1 | 0 | 0 | 0 | 1 | 0 |
| CCCC | 0 | 0 | 0 | 1 | 0 | 0 | 0 | 1 |

| Barcode | Cycle 3 | | | | Cycle 4 | | | |
|---|---|---|---|---|---|---|---|---|
| | A | C | T | G | A | C | T | G |
| TTTT | 1 | 0 | 0 | 0 | 1 | 0 | 0 | 0 |
| GGGG | 0 | 1 | 0 | 0 | 0 | 1 | 0 | 0 |
| AAAA | 0 | 0 | 1 | 0 | 0 | 0 | 1 | 0 |
| CCCC | 0 | 0 | 0 | 1 | 0 | 0 | 0 | 1 |

The cDNA library is prepared for sequencing by attaching adapter sequences to the 5' and 3' ends of the cDNA polynucleotides to generate a sequencing library. The sequencing library is applied to a sequencing array surface containing DNA oligonucleotides attached to the surface. The DNA oligonucleotides include sequences that hybridize to the adapter regions of the cDNA molecules. Sequencing colonies are formed by bridge amplification, which generates copies of the cDNA molecules and complements of the cDNA molecules.

A sequencing primer is applied to the sequencing surface, which hybridizes to adapter regions at the 3' end of the cDNA molecule complements. The barcode regions are questioned using a flow sequencing method, with the order of the applied nucleotides configured so that all barcodes across the sequencing library are sequenced before the primer is extended into the homopolymer region. Briefly, a DNA polymerase is applied to the sequencing surface, a first solution containing a first nucleotides (e.g., deoxy-A, deoxy-G, or deoxy-C), such as non-terminating nucleotides, is applied, and then the sequencing surface is washed to remove unincorporated nucleotides using a wash buffer. The nucleotides contain about 2.5% fluorescently labeled and about 97.5% unlabeled nucleotides. The presence or absence of base incorporation across the colonies is detected using a fluorescence detector. This process is repeated using a second, third, and fourth solution, each containing a different (i.e., second, third, and fourth) nucleotides, in addition to the first solution, to complete a flow cycle. Multiple flow cycles are used (which may be asymmetric) to sequence the barcode region. The nucleotides in the second and third solutions contain about 2.5% fluorescently labeled and about 97.5% unlabeled nucleotides.

The primer is extended during sequencing of the barcode regions to the homopolymer regions, but the barcode regions and the order of discretely applied nucleotides are designed such that the timing of the primer reaching the homopolymer region is controlled. Once the sequencing primer is extended through the barcode region and to the start of the homopolymer region, a fifth solution containing 100% unlabeled thymidine triphosphate is applied to the sequencing surface, which initiates extension of the primer through the homopolymer region. The surfaces are allowed to react for a period of time before the surface is washed with a wash buffer and the process repeated to eliminate stalled primer extension. This allows the primer to be extended through the poly-A homopolymer region and to the start of the target region of the cDNA molecule complements.

The first, second, third, and fourth solutions are then used to sequence the target region of the target region. The solutions are separately applied to the sequencing surface, the surface washed, and presence or absence of base incorporation detected before applying the next solution in a cycle, for a series of cycles.

Example 4

Sample cells are lysed using a lysis buffer, and liquid lysate separated using centrifugation. The separated liquid lysate is incubated with capture beads, each capture bead containing DNA oligomer containing a barcode region (containing a common sample barcode and a UMI) fused to the 5' end of a poly-T region containing 10-30 consecutive thymine bases. mRNA molecules in the liquid lysate are isolated using the capture beads by separating and washing the capture beads. The mRNA molecules are reverse transcribed using the capture probe DNA oligomer and a reverse transcriptase, yielding a cDNA library. Each cDNA molecule in the cDNA library includes the barcode region with a sample barcode and a UMI, a homopolymer poly-T region, and a target region complementary to the mRNA region of interest (which includes at least a portion of a coding region).

The cDNA library is prepared for sequencing by attaching adapter sequences to the 5' and 3' ends of the cDNA polynucleotides to generate a sequencing library. The sequencing library is applied to a sequencing array surface containing DNA oligonucleotides attached to the surface. The DNA oligonucleotides include sequences that hybridize to the adapter regions of the cDNA molecules. Sequencing colonies are formed by bridge amplification, which generates copies of the cDNA molecules and complements of the cDNA molecules.

A first sequencing primer is applied to the sequencing surface, which hybridizes to an adapter region at the 3' end of the cDNA molecule complements. A DNA polymerase is applied to the sequencing surface. A first solution containing a first nucleotides (e.g., deoxy-A, deoxy-G, deoxy-C, or deoxy-T), which may be non-terminating nucleotides, and the sequencing surface is washed to remove unincorporated nucleotides using a wash buffer. The nucleotides contain about 2.5% fluorescently labeled and about 97.5% unlabeled nucleotides. The presence or absence of base incorporation across the colonies is detected using a fluorescence detector. This process is repeated using a second, third, and fourth solutions, each containing a different (i.e., second, third, and fourth) nucleotides to complete a flow cycle, and the flow cycles are repeated to sequence the barcode region. The nucleotides in the second and third solutions contain about 2.5% fluorescently labeled and about 97.5% unlabeled nucleotides.

A second sequencing primer is applied to the sequencing surface, which includes a poly-T homopolymer region and a 5' anchor containing a variable base other than thymine (i.e., A, C, or G). That is, the second sequencing primer is actually a mixture of three different primers with different sequences, with the differences defined only by the variable base at the 5' end of the primer. The second sequencing primer hybridizes to the homopolymer region of the cDNA complement, with the 5' anchor hybridizing to the first base of the target region. The first, second, third and fourth solutions are used to extend the second sequencing primer and sequence the target region of the cDNA molecule complement. The solutions are separately applied to the sequencing surface, the surface washed, and presence or absence of base incorporation detected before applying the next solution in a cycle, for a series of cycles.

Even though the barcode region and the target region are sequencing using separate primers, the sequences can be associated based on the spatial coordinate on the sequencing surface.

Example 5

Sample cells are lysed using a lysis buffer, and liquid lysate separated using centrifugation. The separated liquid lysate is incubated with capture beads, each capture bead containing DNA oligomer containing a barcode region (containing a common sample barcode and a UMI) fused to the 5' end of a poly-T region containing 10-30 consecutive thymine bases. mRNA molecules in the liquid lysate are isolated using the capture beads by separating and washing the capture beads. The mRNA molecules are reverse transcribed using the capture probe DNA oligomer and a reverse transcriptase, yielding a cDNA library. Each cDNA molecule in the cDNA library includes the barcode region with a sample barcode and a UMI, a homopolymer poly-T region, and a target region complementary to the mRNA region of interest (which includes at least a portion of a coding region).

The cDNA library is prepared for sequencing by attaching adapter sequences to the 5' and 3' ends of the cDNA polynucleotides to generate a sequencing library. The sequencing library is applied to a sequencing array surface containing DNA oligonucleotides attached to the surface. The DNA oligonucleotides include sequences that hybridize to the adapter regions of the cDNA molecules. Sequencing colonies are formed by bridge amplification, which generates copies of the cDNA molecules and complements of the cDNA molecules.

A sequencing primer is applied to the sequencing surface, which includes a first primer segment that hybridizes to an adapter region at the 3' end of the cDNA molecule complements, and a second primer segment that hybridizes to the homopolymer region of the cDNA molecule complements. Separating the first primer segment and the second primer segment is a uracil RNA moiety. A first solution containing 100% unlabeled thymidine triphosphate s applied to the sequencing surface, which extends the second primer segment to the end of the homopolymer region of the cDNA molecule complements. Unincorporated nucleotides are then removed by washing the sequencing surface with a wash buffer.

A second solution containing a nucleotides (e.g., deoxy-A, deoxy-G, or deoxy-C) is applied to the sequencing surface, and the sequencing surface is washed to remove unincorporated nucleotides using a wash buffer. The nucleotides contain about 2.5% fluorescently labeled and about 97.5% unlabeled nucleotides. The presence or absence of base incorporation across the colonies is detected using a fluorescence detector. This process is repeated using a third, fourth, and fifth solutions, each containing a different nucleotides to complete a flow cycle, and the flow cycles are repeated to sequence the target region. Although the second solution does not contain thymine, any one of the third, fourth, or fifth could contain the thymine base. The nucleotides in the second and third solutions contain about 2.5% fluorescently labeled and about 97.5% unlabeled nucleotides.

The primer is cleaved by applying a sixth solution containing the uracil-specific excision reagent (USER®) enzyme (available from New England BioLabs), which specifically cuts the uracil moiety between the first and second primer segments. The cleavage solution is then removed using the wash buffer.

The second, third, fourth, and fifth solutions are then used to extend the first primer segment and sequence the barcode region of the cDNA molecule complements. The solutions are separately applied to the sequencing surface, the surface washed, and presence or absence of base incorporation detected before applying the next solution in a cycle, for a series of cycles.

Even though the barcode region and the target region are sequencing using separate primers, the sequences can be associated based on the spatial coordinate on the sequencing surface.

Example 6

Three synthetic test sequences were sequenced using a non-terminating sequencing-by-synthesis method. The test cDNA sequences included an initiation region, a barcode region, a homopolymer region (C-C), and a region of interest. See FIG. 8A. The barcode region of sequence 3 included homopolymers (e.g., a T-T-T homopolymer at flow number 14, a G-G-G homopolymer at flow 16, an A-A-A homopolymer at flow 18 and an A-A-A-A-A homopolymer at flow 30), but these homopolymers are distinct from the C-C homopolymer region. Different flow orders of the nucleotides were used to sequence (1) the initiation region (using a T-A-C-G flow order, 2 cycles), (2) the barcode region (using a T-C-A flow order, 9 cycles), and (3) the homopolymer region and region of interest (using a flow order of G-A-T-C, 2 cycles). The barcode was designed to omit C nucleotides, which were included in the homopolymer region. Therefore, the flow order used to sequence the barcode omitted complementary G nucleotides. Further, the flow order used to sequence the homopolymer region and the region of interest was design to start with a G nucleotide to sequence through the homopolymer region before sequencing the region of interest.

Figure 8:
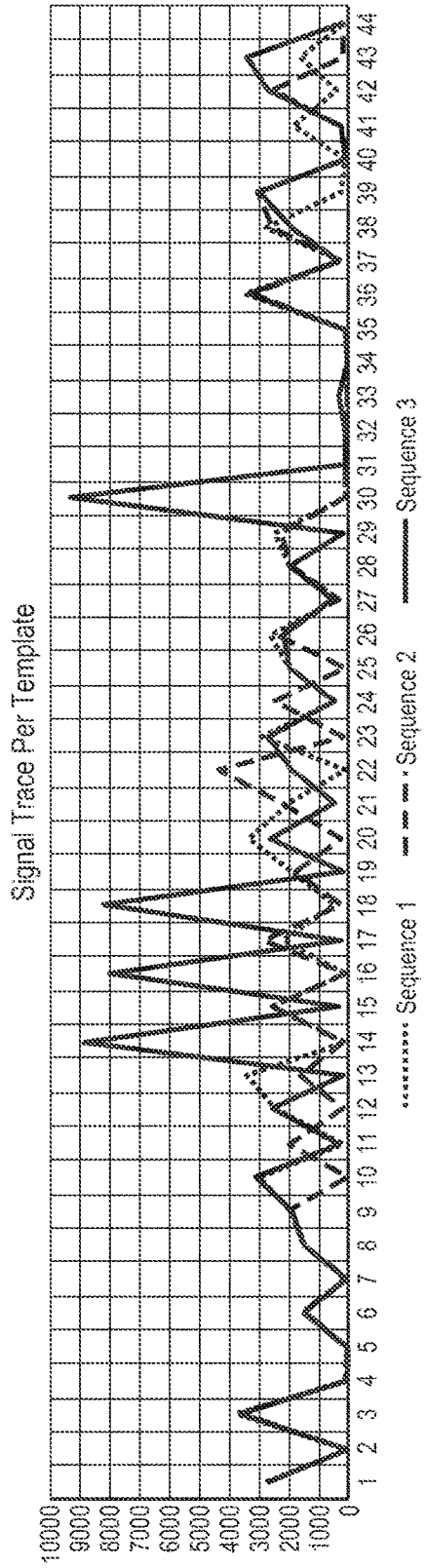
FIG. 8 shows a sequencing flow matrix and a signal trace for three exemplary sequences that include a barcode region, a homopolymer region, and a region of interest.

FIG. 8 shows a flow matrix of the resulting sequencing data for each of the three sequences at each flow position. The data is provided based on the nucleotides flowed into the sequencing reaction, which are complementary to the nucleotides of the sequenced molecule. Below the flow matrix is the signal trace for each sequenced molecule. A greater signal intensity at any given position indicates a larger number of nucleotides incorporated at the indicated flow position.

The barcodes of all three sequences were successfully sequenced in flow numbers 9-30. The barcode flow cycle continued through flows 31-35, but the barcodes had been fully sequenced and no nucleotides were incorporated during these flows. This occurred even at flow number 30 of sequence 3, which included incorporation of five contiguous T nucleotides (no additional T nucleotides were incorporated at position 33). At flow 36, G nucleotides were introduced, which allowed extension of the sequencing strand through the homopolymer region (C-C). The added benefit of this scheme is that sequencing of all three sequences synchronized at flow 36.

What is claimed is:

1. A method of determining a sequence of a region of interest from an mRNA molecule, comprising:

hybridizing a plurality of polynucleotides derived from mRNA with a primer to form a plurality of hybridized templates, the polynucleotides comprising a barcode region, a homopolymer region comprising a plurality of contiguous and identical bases, and a target region comprising a sequence associated with a region of interest from an mRNA molecule, and wherein the target region is uniquely associated with the barcode region;

determining the sequence of the barcode region using labeled nucleotides in a plurality of predetermined cycles, wherein the predetermined cycles and the barcode regions of the polynucleotides are configured such that the primer is extended to the end of the barcode region across the plurality of polynucleotides before being extended into the homopolymer region;

extending the primer within the homopolymer region using unlabeled nucleotides; and determining the sequence of the target region using labeled nucleotides.

2. The method of claim 1, wherein the labeled nucleotides used to determine the sequence of the barcode region comprise non-terminating labeled nucleotides.

3. The method of claim 1, wherein the unlabeled nucleotides used to extend the primer within the homopolymer region comprise non-terminating unlabeled nucleotides.

4. The method of claim 1, wherein the labeled nucleotides used to determine the sequence of the barcode region are mixed with unlabeled nucleotides of the same base.

5. The method of claim 1, further comprising repeating the extending of the primer within the homopolymer region using unlabeled nucleotides one or more times until the primer is extended to the end of the homopolymer region, wherein unincorporated nucleotides are removed prior to repeating the extending.

6. The method of claim 1, wherein different bases of the labeled nucleotides used to determine the target region are discretely used.

7. The method of claim 1, wherein the bases in the homopolymer region of the polynucleotides are adenine or thymine bases.

8. The method of claim 1, wherein the homopolymer region of the polynucleotides comprises as least 8 contiguous and identical bases.

9. The method of claim 1, wherein the polynucleotides are cDNA molecules.

10. The method of claim 1, wherein the region of interest of the mRNA molecule comprises a coding region.

11. The method of claim 1, wherein the labeled nucleotides used in determining the sequence of the target region comprise non-terminating labeled nucleotides.

12. The method of claim 1, wherein 50% or fewer of the nucleotides used in determining the sequence of the barcode region or determining the sequence of the target region are labeled.

13. The method of claim 1, wherein 0.1% or fewer of the nucleotides used in extending the primer within the homopolymer region are labeled.

14. The method of claim 1, wherein all of the nucleotides used in extending the primer within the homopolymer region are unlabeled.

15. The method of claim 1, wherein different bases of the labeled nucleotides used to determine the barcode region are discretely used.

16. The method of claim 1, wherein the homopolymer region of the polynucleotides comprises as least 50 contiguous and identical bases.

17. The method of claim 1, wherein the barcode region comprises a sample barcode.

18. The method of claim 10, further comprising associating the determined sequence of the barcode region with the determined sequence associated with the mRNA coding region from the same target nucleic acid molecule.

19. The method of claim 1, wherein the region of interest of the mRNA molecule comprises a 3'-untranslated region or a 5'-untranslated region of the mRNA molecule.

20. The method of claim 1, wherein the labeled nucleotides used to determine the sequence of the target region are mixed with unlabeled nucleotides of the same base.

* * * * *